United States Patent
Weissensteiner et al.

(10) Patent No.: US 6,777,567 B2
(45) Date of Patent: Aug. 17, 2004

(54) FERROCENYL DIPHOSPHINES AND THEIR USE

(75) Inventors: Walter Weissensteiner, Mödling (AT); Thomas Sturm, Vienna (AT); Felix Spindler, Starrkirch-Wil (CH)

(73) Assignee: Solvias AG, Basel (CH)

( * ) Notice: Subject to any disclaimer, the term of this patent is extended or adjusted under 35 U.S.C. 154(b) by 0 days.

(21) Appl. No.: 10/312,816

(22) PCT Filed: Jul. 2, 2001

(86) PCT No.: PCT/EP01/07529

§ 371 (c)(1),
(2), (4) Date: Dec. 31, 2002

(87) PCT Pub. No.: WO02/02578

PCT Pub. Date: Jan. 10, 2002

(65) Prior Publication Data
US 2003/0212284 A1 Nov. 13, 2003

(51) Int. Cl.[7] .................. C07F 17/02; B01J 31/00; C07C 5/00
(52) U.S. Cl. .................. 556/16; 556/14; 556/21; 502/154; 502/155; 585/274; 585/276; 585/277
(58) Field of Search .................. 556/14, 16, 21; 502/154, 155; 585/274, 276, 277

(56) References Cited

U.S. PATENT DOCUMENTS

| | | | |
|---|---|---|---|
| 5,371,256 A | 12/1994 | Togni et al. | 556/14 |
| 5,466,844 A | 11/1995 | Spindler et al. | 556/11 |
| 5,583,241 A | 12/1996 | Spindler et al. | 556/11 |
| 6,191,284 B1 * | 2/2001 | Knochel et al. | 548/402 |

OTHER PUBLICATIONS

Ireland et al., entitled "*Ferrocenylliganden mit zwei Phosphanylsubstituenten in a, e–Position für die Übergangsmetall–katalysierte asymmetrische Hydrierung funktionalisierter Doppelbindungen*", Angewandte Chemie, vol. 111, No. 21, 1999, pp. 3397–3400, XP002179596.

\* cited by examiner

Primary Examiner—Porfirio Nazario-Gonzalez
(74) Attorney, Agent, or Firm—Wenderoth, Lind & Ponack, L.L.P.

(57) ABSTRACT

Compounds of the formula (I) and (Ia) in the form of racemates, mixtures of diastereomers or in essentially enantiomerically pure form, (I), (Ia), where R is hydrogen, $C_1$–$C_8$alkyl, $C_5$–$C_{12}$cycloakyl, phenyl or phenyl substituted by from 1 to 3 $C_1$–$C_4$alky or $C_1$–$C_4$alkoxy groups; n is 0 or an integer from 1 to 4 and $R^1$ are identical or different substituents selected from the group consisting of $C_1$–$C_4$alkyl, $C_1$–$C_4$fluoroalkyl and $C_1$–$C_4$alkoxy; $X_1$ and $X_2$ are each, independently of one another, secondary phosphino; T is $C_6$–$C_{20}$arylene or $C_3$–$C_{16}$heteroarylene; and $X_2$ is bound in the ortho position relative to the T-cyclopentadienyl bond. The compounds are ligands for complexes of metal selected from transition groups (I) and (VIII) of the Periodic Table of the Elements, and these metal complexes are valuable catalysts for the asymmetric addition of hydrogen, boron hydrides or silanes onto carbon-carbon or carbon-heteroatom multiple bonds in prochiral organic compounds or the asymmetric addition of carbon nucleophiles or amines onto allyl compounds.

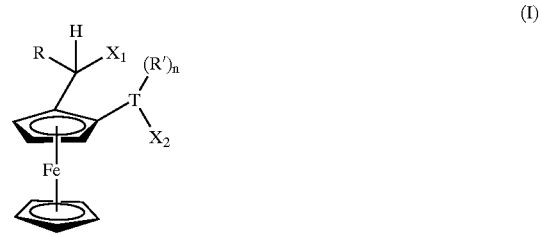

(I)

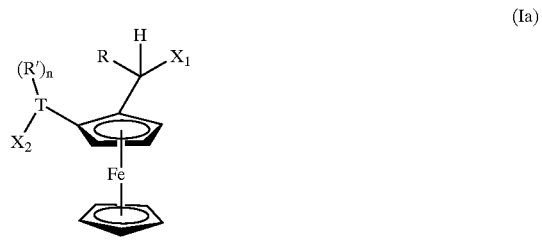

(Ia)

32 Claims, No Drawings

FERROCENYL DIPHOSPHINES AND THEIR USE

The present invention relates to 1-(α-secondary-phosphinoalkyl)-2-(secondary-phosphinoaryl) ferrocenyls; a process for preparing these ferrocenyl diphosphines and intermediates; metal complexes comprising metals selected from transition groups I and VIII of the Periodic Table of the Elements (d-10 and d-8 metals, hereinafter referred to as TM8 metals) and these ferrocenyl disphosphines; a process for asymmetric synthesis by addition of hydrogen, borohydrides or silanes onto a carbon-carbon or carbon-heteroatom multiple bond in prochiral organic compounds or addition of carbon nucleophiles, alcohols or amines onto allylic compounds, and particularly for the asymmetric hydrogenation of carbon-carbon or carbon-heteroatom multiple bonds by means of hydrogen, in the presence of catalytic amounts of the metal complexes; and the use of the metal complexes as catalysts for asymmetric synthesis by addition of hydrogen, borohydrides or silanes onto carbon-carbon or carbon-heteroatom multiple bonds in prochiral organic compounds or of carbon nucleophiles, alcohols or amines onto allylic compounds, and particularly for the asymmetric hydrogenation of carbon-carbon or carbon-heteroatom multiple bonds by means of hydrogen.

U.S. Pat. Nos. 5,371,256, 5,446,844 and 5,583,241 describes $C_2$-symmetric 1-(α-secondary-phosphinoalkyl)-2-secondary-phosphinoferrocenyls as ligands for metal complexes which are, inter alia, excellent homogeneous catalysts for the asymmetric hydrogenation of organic compounds having multiple bonds.

In Angew. Chem. 1999, 111, No. 21, pages 3397 to 3400, T. Ireland et al. disclose $C_2$-symmetric 1-[α-(2'-secondary-phosphinophen-1'-yl-alkyl)]-2-secondary-phosphinoferrocenyls as ligands for metal complexes; the ruthenium and rhodium complexes of these ligands are effective catalysts in the enantioselective hydrogenation of β-keto esters or β-ketones or of methyl α-acetamidocinnamate or dimethyl itaconate.

It has now surprisingly been found that $C_1$-symmetric secondary diphosphines having a ferrocenyl-aryl skeleton are valuable ligands for TM8 metal complexes which are excellent homogeneous catalysts for asymmetric syntheses, particularly for the asymmetric hydrogenation of carbon-carbon and carbon-heteroatom multiple bonds. A particular advantage of the ligands is that excellent enantioselectivities are retrieved when using prochiral carboxylic acids.

The invention firstly provides compounds of the formulae I and Ia in the form of racemates, mixtures of diastereomers or in essentially enantiomerically pure form,

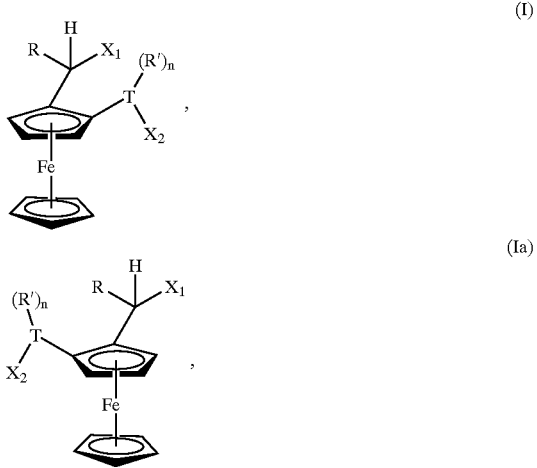

where

R is hydrogen, $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups;

n is 0 or an integer from 1 to 4 and R' are identical or different substituents selected from the group consisting of $C_1$–$C_4$alkyl, $C_1$–$C_4$fluoroalkyl and $C_1$–$C_4$alkoxy;

$X_1$ and $X_2$ are each, independently of one another, secondary phosphino;

T is $C_6$–$C_{20}$arylene or $C_3$–$C_{16}$heteroarylene;

and $X_2$ is bound in the ortho position relative to the T-cyclopentadienyl bond.

Preference is given to compounds of the formulae Ib and Ic in the form of racemates, mixtures of diastereomers or in essentially enantiomerically pure form,

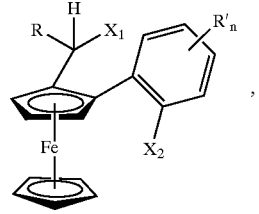

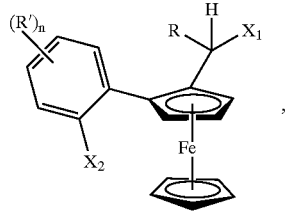

where

R is hydrogen, $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups;

n is 0 or an integer from 1 to 4 and R' are identical or different substituents selected from the group consisting of $C_1$–$C_4$alkyl, $C_1$–$C_4$fluoroalkyl and $C_1$–$C_4$alkoxy, or two substituents R' form the group —CH=CH—CH=CH— which may be unsubstituted or substituted by $C_1$–$C_4$alkyl or $C_1$–$C_4$alkoxy; and $X_1$ and $X_2$ are each, independently of one another secondary phosphino.

An alkyl group R is preferably a linear $C_1$–$C_4$alkyl, for example methyl, ethyl, propyl, butyl, pentyl, hexyl, heptyl or octyl. Preferred alkyls are ethyl and, in particular, methyl.

A cycloalkyl group R is preferably $C_5$–$C_6$cycloalkyl, for example cyclopentyl or cyclohexyl.

An arylene group T preferably contains from 6 to 14 carbon atoms. Examples of arylene are phenylene, naphthylene, anthracylene and phenanthrylene. Preference is given to phenylene and naphthylene.

A heteroarylene group T preferably contains from 5 to 14 carbon atoms. The heteroatoms are preferably selected from the group consisting of O, S and N. The heteroarylene can contain from 1 to 4, preferably 1 or 2, identical or different heteroatoms. A few examples are pyridinylene, pyrimidinylene, pyrazinylene, pyrrolylene, furanylene, oxazolylene, imidazolylene, benzofuranylene, indolylene, benzimidazolylene, quinolylene, isoquinolylene, quinazolinylene and quinoxalinylene.

Examples of phenyl substituted by from 1 to 3 $C_1$–$C_4$alkyl or $C_1$–$C_4$alkoxy groups as R are tolyl, xylyl, trimethylphenyl, methoxyphenyl, ethoxyphenyl and dimethoxyphenyl.

R is preferably hydrogen, $C_1$–$C_4$alkyl, cyclopentyl, cyclohexyl or phenyl. R is very particularly preferably hydrogen, methyl, ethyl, n-propyl or n-butyl.

When R is a substituent, the compounds preferably correspond to the formula Id or Ie,

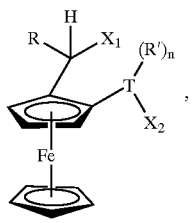

(Id)

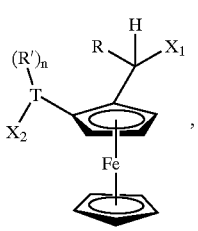

(Ie)

where T, R, R', n, $X_1$ and $X_2$ are as defined above.

When R is a substituent, the compounds particularly preferably correspond to the formula If or Ig,

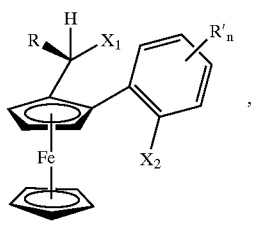

(If)

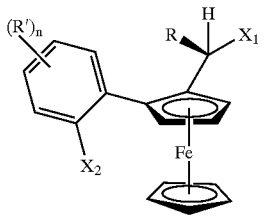

(Ig)

where R, R', n, $X_1$ and $X_2$ are as defined above.

An alkyl group R' preferably contains 1 or 2 carbon atoms. Preference is given to linear alkyl. Examples of alkyl groups R' are methyl, ethyl, n- and i-propyl, n-, i- and t-butyl. Preference is given to methyl and ethyl and particular preference is given to methyl.

Alkoxy groups R' preferably contain 1 or 2 carbon atoms. Preference is given to linear alkoxy. Examples of alkoxy groups R' are methoxy, ethoxy, n- and i-propoxy, n-, i- and t-butoxy. Preference is given to methoxy and ethoxy and particular preference is given to methoxy.

A fluoroalkyl group R' is preferably trifluoromethyl.

In the formulae I to Ie, n is preferably 0, 1 or 2, particularly preferably 0 or 1.

The individual phosphine groups $X_1$ and $X_2$ may contain two identical or two different hydrocarbon radicals, or the two hydrocarbon radicals together with the P atom can form a three- to eight-membered ring. The individual phosphine groups preferably contain two identical hydrocarbon radicals, and different phosphine groups of this type may be bound to the ferrocenyl skeleton. The hydrocarbon radicals may be unsubstituted or substituted and may contain from 1 to 22, preferably from 1 to 12, carbon atoms. Among the compounds of the formula I, particular preference is given to ones in which the individual phosphine groups contain two identical or different radicals selected from the group consisting of linear or branched $C_1$–$C_{12}$alkyl; unsubstituted or $C_1$–$C_6$alkyl- or $C_1$–$C_6$alkoxy-substituted $C_5$–$C_{12}$cycloalkyl or $C_5$–$C_{12}$cycloalkyl-$C_2$—; phenyl or benzyl; or phenyl or benzyl substituted by halogen (for example F, Cl and Br), $C_1$–$C_6$alkyl, $C_1$–$C_6$haloalkyl (for example trifluoromethyl), $C_1$–$C_6$alkoxy, $C_1$–$C_6$haloalkoxy (for example trifluoromethoxy), $(C_6H_5)_3$Si, $(C_1$–$C_{12}$alkyl$)_3$Si, secondary amino or —$CO_2$—$C_1$–$C_6$alkyl (for example —$CO_2CH_3$).

The two radicals in the phosphine groups can together also be unsubstituted or halogen-, $C_1$–$C_6$-alkyl- or $C_1$–$C_6$-alkoxy-substituted dimethylene, trimethylene, tetramethylene or pentamethylene. The substituents are preferably bound in the two ortho positions relative to the P atoms.

The phosphine groups can also be groups of the formulae

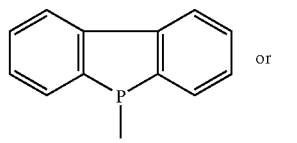

or

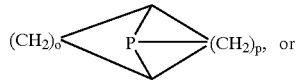

or

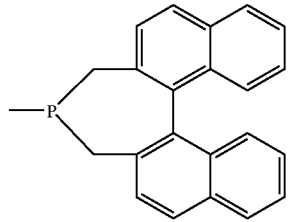

where o and p are each, independently of one another, an integer from 2 to 10, and the sum o+p is from 4 to 12, preferably from 5 to 8, and the phenyl rings are unsubstituted or substituted by $C_1$–$C_4$-alkyl and $C_1$–$C_4$-alkoxy. Examples are [3.3.1]phobyl and [4.2.1]phobyl of the formulae

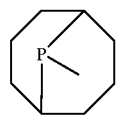 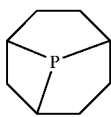

Examples of secondary phosphine groups in which the two hydrocarbon radicals together with the P atom form a 3- to 8-membered ring are, in particular, groups of the formula

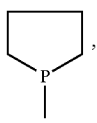

which may be substituted by $C_1$–$C_4$alkyl or $C_1$–$C_4$alkoxy in one or both ortho positions and possibly the meta positions relative to the P atom.

Examples of alkyl substituents on P, which preferably contain from 1 to 6 carbon atoms, are methyl, ethyl, n-propyl, i-propyl, n-butyl, i-butyl, t-butyl, and the isomers of pentyl and hexyl. Examples of unsubstituted or alkyl-substituted cycloalkyl as substituent on P are cyclopentyl, cyclohexyl, methylcyclohexyl and ethylcyclohexyl and dimethylcyclohexyl. Examples of alkyl-, alkoxy-, haloalkyl- and haloalkoxy-substituted phenyl and benzyl substituents on P are methylphenyl, dimethylphenyl, trimethylphenyl, ethylphenyl, methylbenzyl, methoxyphenyl, dimethoxyphenyl, trifluoromethylphenyl, bis(trifluoromethyl)phenyl, tris(trifluoromethyl)phenyl, trifluoromethoxyphenyl and bis(trifluoromethoxy)phenyl.

Preferred phosphine groups are ones which contain identical or different, preferably identical, radicals selected from the group consisting of $C_1$–$C_6$alkyl, unsubstituted cyclopentyl or cyclohexyl or cyclopentyl or cyclohexyl substituted by from 1 to 3 $C_1$–$C_4$alkyl or $C_1$–$C_4$alkoxy groups, benzyl and particularly phenyl which may be unsubstituted or substituted by from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

In the compounds of the formulae I to Ie, $X_1$ is preferably the group —$PR_1R_2$ and $X_2$ is preferably the group —$PR_3R_4$, where $R_1$, $R_2$, $R_3$ and $R_4$ are each, independently of one another, a hydrocarbon radical which has from 1 to 20 carbon atoms and is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3$Si, $(C_1$–$C_{12}$-alkyl$)_3$Si, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

$R_1$, $R_2$, $R_3$ and $R_4$ are preferably identical or different, in particular identical, radicals selected from the group consisting of branched $C_3$–$C_6$alkyl, unsubstituted cyclopentyl and cyclohexyl, cyclopentyl and cyclohexyl substituted by from one to three $C_1$–$C_4$alkyl or $C_1$–$C_4$alkoxy groups, unsubstituted benzyl and benzyl substituted by from one to three $C_1$–$C_4$alkyl or $C_1$–$C_4$alkoxy groups, and in particular, unsubstituted phenyl and phenyl substituted by from one to three $C_1$–$C_4$alkyl, $C_1$–$C_4$alkoxy, —$NH_2$, OH, F, Cl, $C_1$–$C_4$fluoroalkyl or $C_1$–$C_4$fluoroalkoxy.

$R_1$, $R_2$, $R_3$ and $R_4$ are particularly preferably identical or different, in particular identical, radicals selected from the group consisting of unsubstituted phenyl and phenyl substituted by from one to three $C_1$–$C_4$alkyl, $C_1$–$C_4$alkoxy or $C_1$–$C_4$fluoroalkyl groups.

A preferred subgroup of the compounds of the invention are those of the formulae If, Ig, Ih and Ii,

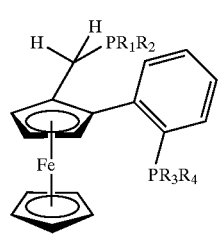

I(f)

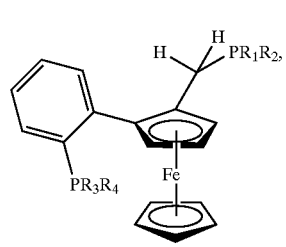

(Ig)

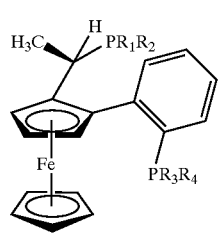

(Ih)

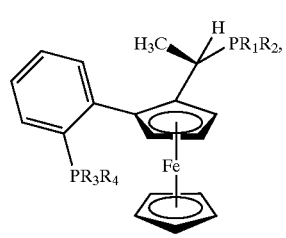

(Ii)

where $R_1$, $R_2$, $R_3$ and $R_4$ are identical or different and are selected from the group consisting of α-branched $C_3$–$C_6$alkyl, unsubstituted $C_5$–$C_7$cycloalkyl and $C_5$–$C_7$cycloalkyl substituted by from one to three $C_1$–$C_4$alkyl or $C_1$–$C_4$alkoxy groups and unsubstituted phenyl and phenyl substituted by from one to three $C_1$–$C_4$alkyl, $C_1$–$C_4$alkoxy and $C_1$–$C_4$fluoroalkyl groups and unsubstituted and $C_1$–$C_4$alkyl- or $C_1$–$C_4$alkoxy-substituted dimethylene, trimethylene, tetramethylene and hexamethylene. In particular, $R_1$ and $R_2$ as well as $R_3$ and $R_4$ or $R_1$, $R_2$, $R_3$ and $R_4$ are identical radicals.

The compounds of the invention can be prepared by reactions described in the literature or by methods analogous thereto. The synthesis can be carried out stereoselectively by selection of appropriately optically pure precursors or intermediates. The desired optically pure compounds can, however, also be obtained by resolution of racemates or separation of mixtures of diastereomers of the intermediates and/or end products.

The invention further provides a process for preparing compounds according to the invention, wherein a) a compound of the formula II

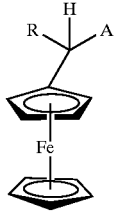

(II)

where R is as defined above and A is secondary amino, is firstly reacted with a lithium alkyl, the reaction mixture is treated with a zinc dihalide, preferably zinc dichloride, and is then reacted in the presence of Pd(0) or Pd(II) complexes, for example $Pd_2(dba)_3$ or Pd(tertiary phosphine)$_2$ dihalides, as catalyst with a compound of the formula

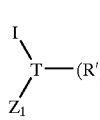 or preferably 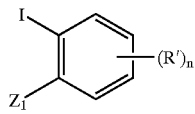

where R' and n are as defined above and $Z_1$ is F, Cl, Br or I, preferably Br, to form a compound of the formula III, preferably IIIa,

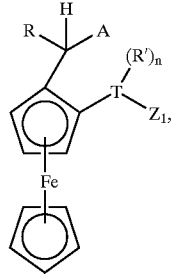

(III)

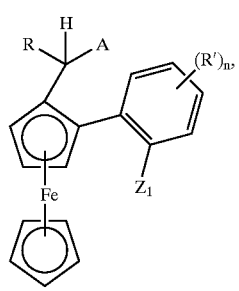

(IIIa)

b) the compound of the formula III or IIIa is reacted firstly with a lithium alkyl and then with a secondary halophosphine $X_2Cl$ or $X_2Br$ (for example of the formulae $R_3R_4PCl$ or $R_3R_4PBr$) to form a compound of the formula IV, preferably IVa, where $X_2$, $R_3$ and $R_4$ are as defined above,

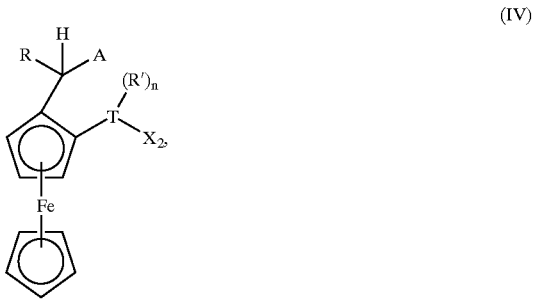

(IV)

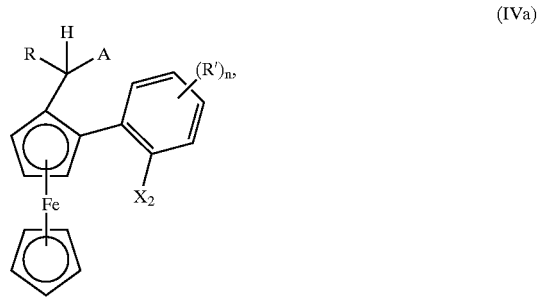

(IVa)

c) the phosphine group of the compound of the formula IV or IVa is oxidised to form a compound of the formula V or Va,

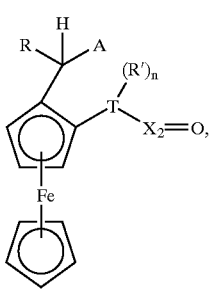

(V)

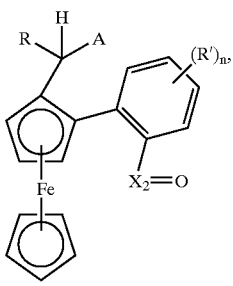

(Va)

d) the oxidised compound of the formula V or Va is reacted in the presence of an acid with a secondary phosphine $X_1H$, where $X_1$ is as defined above (for example with a phosphine of the formula $R_1R_2PH$), to form a compound of the formula VI, preferably VIa,

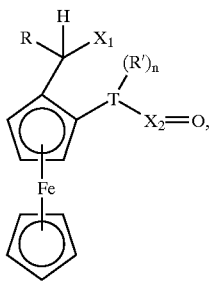

(VI)

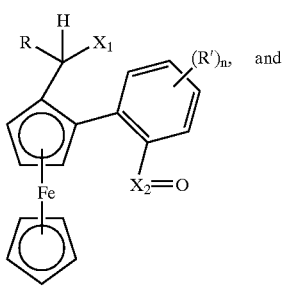

(VIa)

e) the $X_2$=O group in the compound of the formula VI or VIa is reduced to give a compound of the formula I or Ia.

Compounds of the formula I in which R is hydrogen can also be prepared by two modified processes. In both processes, a chiral reagent is used, in a first variant to be able to carry out separation of the diastereomers, and in a second variant to be able to carry out a reaction step with high diastereoselectivity.

In the first variant, the secondary amino group of a compound of the formula VII, preferably VIIa, (VII)

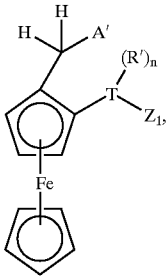

(VIIa)

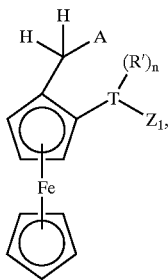

prepared by a method analogous to process step a) is reacted with an alkyl halide, for example methyl iodide, to form an alkyl ammonium halide, the alkyl ammonium halide group is then replaced by a chiral secondary amine, for example α-methoxypyrrolidine or O-methylephedrine, the mixture of diastereomers of the resulting compound of the formula VII, preferably VIIIa, (VIII)

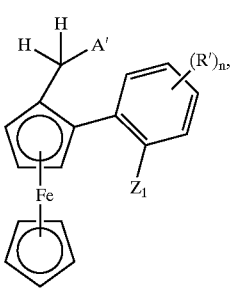

(VIIIa)

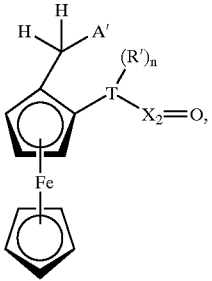

where A' is a chiral secondary amino group, is separated, the isolated diastereomer is reacted in a manner analogous to process step b) with a compound of the formula $ClX_2(O)$, for example $ClP(O)R_3R_4$, to form a compound of the formula IX or IXa, preferably IXb or IXc, (IX)

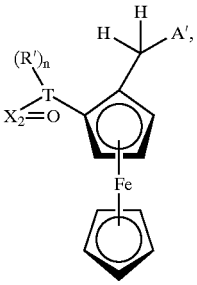

(IXa)

(IXb)
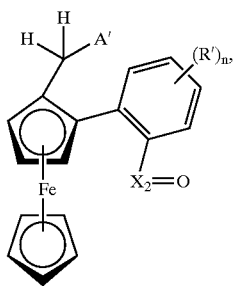

(IXc)
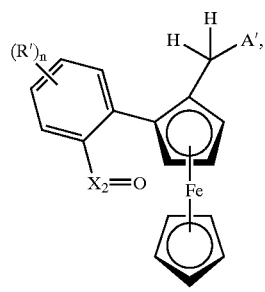

the compound of the formula IX or IXa, preferably IXb or IXc, is reacted in the presence of an alkyl halide with a secondary amine AH to convert it into a compound of the formula X or Xa, preferably Xb or Xc, (X)
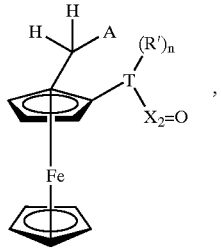

(Xa)
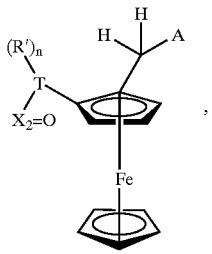

(Xb)
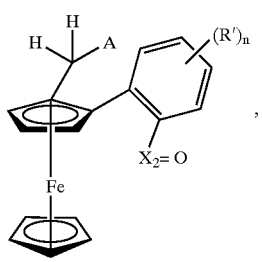

(Xc)
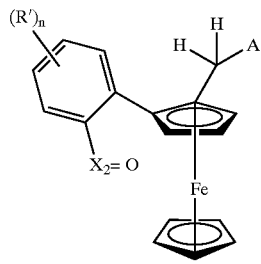

the compound of the formula X or Xa, preferably Xb or Xc, is reacted with a secondary phosphine $X_1H$, for example $HPR_1R_2$, in a manner analogous to process step d) to form a compound of the formula XI or XIa, preferably XIb or XIc, (XI)
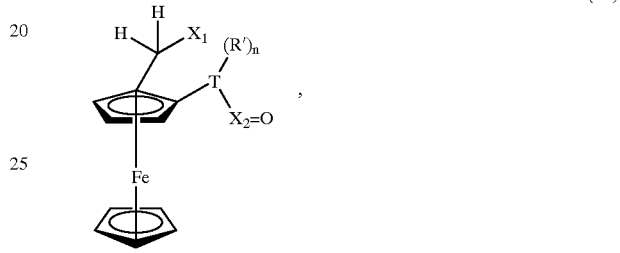

(XIa)
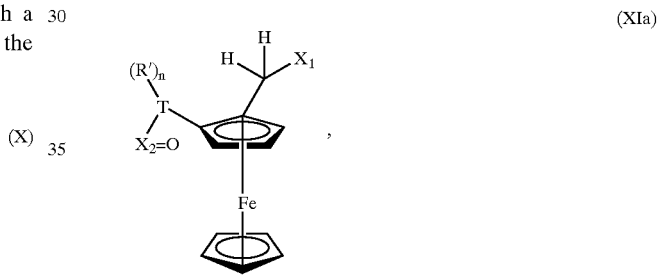

(XIb)
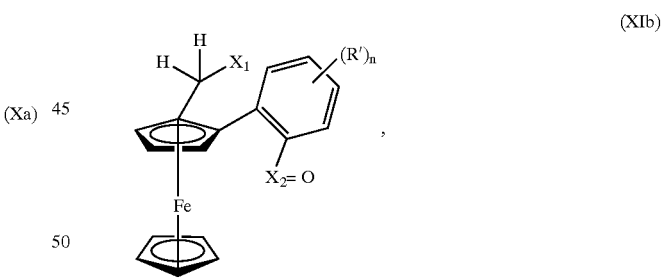

(XIc)
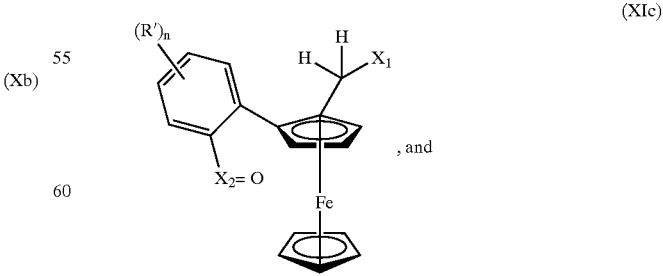

, and the compound of the formula XI or XIa, preferably XIb or XIc, is then reduced to give a compound of the formula I or Ia, preferably Ib or Ic, in which R is hydrogen.

In a second variant, a compound of the formula II is reacted with an alkyl halide, preferably methyl iodide, to give the corresponding alkyl ammonium compound which is converted in the presence of a chiral amine auxiliary reagent, for example O-methylephedrine, into a compound in which the secondary amino group is replaced by the amine auxiliary reagent.

This intermediate is reacted with a lithium alkyl, for example sec-butyllithium, and then with iodine. The iodated ferrocene compound can be reacted as described above, either directly or after replacement of the chiral amine auxiliary reagent with a secondary amine, for example, dimethylamine, with 1-bromo-2-iodarylene or 1-bromo-2-iodheteroarylene, preferably 1-bromo-2-iodbenzene, to form a compound of the formula

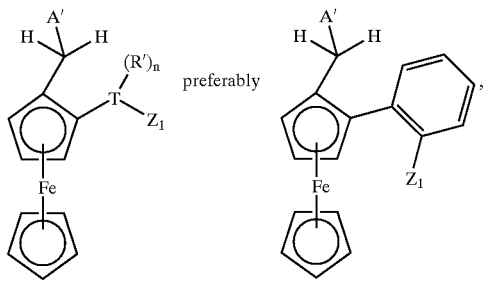

where $Z_1$ is as defined above and A' is secondary amino or the amine radical of a chiral amine auxiliary reagent. A significant advantage of this variant is that the diastereoselectivities are very high and can be up to 98%. The introduction of the phosphino groups can then be carried out as described above.

The individual process steps are known per se and are illustrated in the examples of preparations. The reactions are advantageously carried out in an inert solvent. Examples of solvents will be given further below. The separation of diastereomers is preferably carried out by chromatography (HPLC or flash chromatography), for which commercially available chiral columns may be employed. The reaction temperatures for the individual process steps are described in the prior art for analogous reactions. The isolation and if appropriate purification of the reaction products can be carried out in a customary manner by means of extraction, crystallisation, distillation and/or chromatography.

The secondary amino group A can be an open-chain or cyclic amine containing, for example, from 2 to 20, preferably from 2 to 12 and particularly preferably from 2 to 8, carbon atoms. The secondary amino group A can contain, for example, linear or branched alkyl, cycloalkyl, cycloalkylalkyl, aryl and/or aralkyl groups, or it can be an N-heterocyclic amino radical which may be unsubstituted or substituted by $C_1$–$C_4$alkyl or $C_1$–$C_4$alkoxy, particularly in an ortho position relative to the N atom. The secondary amino group A can, for example, have the formula XII,

—$NR_5R_6$ (XII), where $R_5$ and $R_6$ are each, independently of one another, $C_1$–$C_{12}$alkyl, preferably $C_1$–$C_6$alkyl, $C_3$–$C_8$cycloalkyl, preferably $C_5$–$C_6$cycloalkyl, $C_3$–$C_8$cycloalkyl-$C_1$–$C_4$alkyl, preferably $C_5$–$C_6$cycloalkyl–$C_1$–$C_3$alkyl, $C_6$–$C_{10}$aryl, preferably phenyl or naphthyl, $C_6$–$C_{14}$aralkyl, preferably phenyl- or naphthyl-$C_1$–$C_3$alkyl, or $R_5$ and $R_6$ together with the N atom form an aliphatic, 3- to 8-membered, preferably 5- or 6-membered, ring, where the cyclic radicals may be unsubstituted or substituted by $C_1$–$C_4$alkyl or $C_1$–$C_4$alkoxy.

Examples of substituents are methyl, ethyl, methoxy and ethoxy.

Alkyl groups $R_5$ and $R_6$ are preferably linear alkyl groups containing from 1 to 4 carbon atoms. Some examples are methyl, ethyl, propyl, butyl, pentyl, hexyl, heptyl, octyl, nonyl, decyl, undecyl and dodecyl. Particular preference is given to methyl and ethyl.

Preferred cycloalkyl groups $R_5$ and $R_6$ are cyclopentyl and cyclohexyl. Preferred cycloalkylalkyl groups $R_5$ and $R_6$ are cyclopentylmethyl, cyclopentylethyl, cyclohexylmethyl and cyclohexylethyl. Preferred $C_6$–$C_{14}$aralkyl groups $R_5$ and $R_6$ are phenylmethyl, naphthylmethyl, phenylethyl and naphthylethyl.

When $R_5$ and $R_6$ together with the N atom form an aliphatic ring, it is preferred that $R_5$ and $R_6$ are together —$(CH_2)_a$—, where a is an integer from 3 to 7, preferably 4 or 5, or $R_5$ and $R_6$ are together 3-oxapentylene.

In the chromatographic separation of diastereomers, the separation efficiency can frequently be improved and optimised if A is a chiral secondary amino A'. A' is then preferably a secondary amino group bearing an α-substituted alkyl or a cyclic secondary amino group substituted in the a position. Preferred α-substituted alkyl groups are α-phenyl- or α-naphthyl-$C_2$–$C_6$alkyl, in particular α-phenylethyl or α-naphthylethyl. Preferred cyclic secondary amino groups are pyrolidinyl groups substituted in the a position relative to the N atom by $C_1$–$C_4$alkyl or $C_1$–$C_4$alkoxy, for example methyl or methoxy.

The invention also provides the intermediates of the formulae XIII and XIIIa and preferably XIIIb and XIIIc in the form of racemates, mixtures of diastereomers or in essentially enantiomerically pure form,

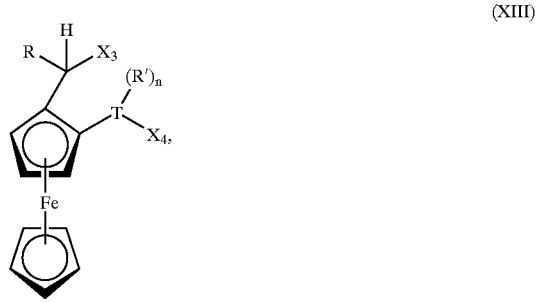

(XIII)

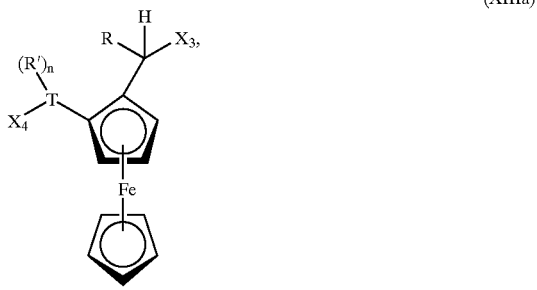

(XIIIa)

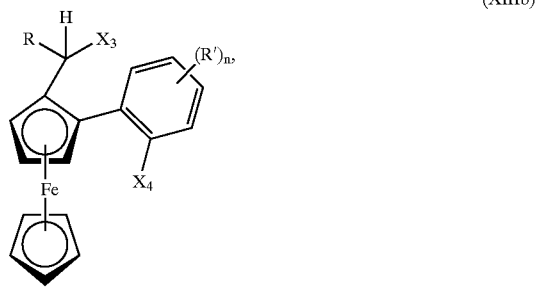

(XIIIb)

-continued

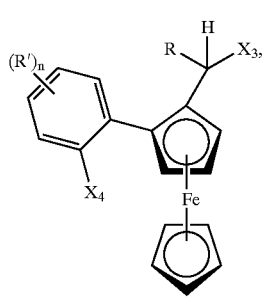

(XIIIc)

where
R is hydrogen, $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups;
n is 0 or an integer from 1 to 4 and R' are identical or different substituents selected from the group consisting of $C_1$–$C_4$alkyl and $C_1$–$C_4$alkoxy; and
a) $X_3$ is a secondary amino group A and $X_4$ is bromine, I or the group $X_2$=O;
b) $X_3$ is a secondary phosphino group $X_1$ and $X_4$ is the group $X_2$=O; or
c) R is $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups, $X_3$ is a secondary amino group A and $X_4$ is the group $X_2$;
$X_2$ is secondary phosphino;
T is $C_6$–$C_{20}$arylene or $C_3$–$C_{16}$heteroarylene;
and $X_2$ is found in the ortho position relative to the T-cyclopentadienyl bond.

Advantageous and preferred meanings of T, R, R', n, A, $X_1$ and $X_2$ are as described above.

The compounds of the formula I provided by the invention are suitable as ligands for complexes of metal selected from the group consisting of TM8 metals; in particular the group consisting of Ru, Rh and Ir, which are excellent catalysts or catalyst precursors for asymmetric syntheses, for example the asymmetric hydrogenation of prochiral unsaturated, organic compounds. If prochiral unsaturated organic compounds are used, a very high excess of optical isomers can be induced in the synthesis of organic compounds and a very high chemical conversion can be achieved in short reaction times. In the case of selected substrates (for example 2-methylcinnamic acid), the enantioselectivity is considerably higher than when using known ditertiary ferrocenyl diphosphines.

The invention further provides complexes of metals selected from the group consisting of the TM8 metals with compounds of the formulae I and Ia and preferably Ib and Ic as ligands.

Examples of suitable metals are Cu, Ag, Au, Ni, Co, Rh, Pd, Ir and Pt. Preferred metals are rhodium and iridium and also ruthenium, platinum and palladium.

Particularly preferred metals are ruthenium, rhodium and iridium.

The metal complexes can, depending on the oxidation state and coordination number of the metal atom, contain further ligands and/or anions. The metal complexes can be cationic. Such analogous metal complexes and their preparation are widely described in the literature.

The metal complexes can, for example, correspond to the formulae XIV and XV, $$A_1MeL_n \text{ (XIV), } (A_1MeL_n)^{(z+)}(E^-)_z \quad\quad \text{(XV),}$$

where $A_1$ is a compound of the formula I or Ia, preferably Ib or Ic,
L are identical or different monodentate, anionic or nonionic ligands, or two L together form identical or different bidentate, anionic or nonionic ligands;
n is 2, 3 or 4 when L is a monodentate ligand, or n is 1 or 2 when L is a bidentate ligand;
z is 1, 2 or 3;
Me is a metal selected from the group consisting of Rh, Ir and Ru, with the metal having an oxidation state of 0, 1, 2, 3 or 4;
$E^-$ is the anion of an oxo acid or complex acid; and
the anionic ligands balance the charge of the metal in the oxidation state 1, 2, 3 or 4.

The above-described preferences and embodiments apply to the compounds of the formulae I, Ia, Ib and Ic.

Monodentate nonionic ligands can, for example, be selected from the group consisting of olefins (for example, ethylene, propylene), allyles (allyl, 2-methallyl), solvating solvents (nitriles, linear or cyclic ethers, unalkylated or N-alkylated amides and lactams, amines, phosphines, alcohols, carboxylic esters, sulphonic esters), nitrogen monoxide and carbon monoxide.

Monodentate anionic ligands can, for example, be selected from the group consisting of halides (F, Cl, Br, I) pseudohalides (cyanide, cyanate, isocyanate) and anions of carboxylic acids, sulphonic acids and phosphonic acids and phosphonic acids (carbonate, formate, acetate, propionate, methylsulphonate, trifluoromethylsulphonate, phenylsulphonate, tosylate).

Bidentate nonionic ligands can, for example, be selected from the group consisting of linear and cyclic diolefins (for example hexadiene, cyclooctadiene, norbornadiene), dinitriles (malononitrile), unalkylated or N-alkylated carboxylic diamides, diamines, diphosphines, diols, acetonylacetonates, dicarboxylic diesters and disulphonic diesters.

Bidentate anionic ligands can, for example, be selected from the group consisting of the anions of dicarboxylic acids, disulphonic acids and diphosphonic acids (for example of oxalic acid, malonic acid, succinic acid, maleic acid, methylenedisulphonic acid and methylenedisphosphonic acid).

Preferred metal complexes also include ones in which E is —$Cl^-$, —$Br^-$, —$I^-$, $ClO_4^-$, $CF_3SO_3^-$, $CH_3SO_3^-$, $HSO_4^-$, $BF_4^-$, $B(phenyl)_4^-$, $B(C_6F_5)_4^-$, $B(3,5$-bistrifluoromethylphenyl$)_4^-$, $PF_6^-$, $SbCl_6^-$, $AsF_6^-$ or $SbF_6^-$.

Particularly preferred metal complexes which are particularly suitable for hydrogenation correspond to the formulae XVI and XVII, $$[A_1Me_1YZ] \text{ (XVI), } [A_1Me_1Y]^+E_1^- \quad\quad \text{(XVII),}$$

where
$A_1$ is a compound of the formula I or Ia, preferably Ib or Ic;
$Me_1$ is rhodium or iridium;
Y is two olefins or one diene;
Z is Cl, Br or I; and
$E_1^-$ is the anion of an oxo acid or complex acid.

The above-described embodiments and preferences apply to the compounds of the formulae I, Ia, Ib and Ic.

Olefins Y can be $C_2$–$C_{12}$ olefins, preferably $C_2$–$C_6$olefins and particularly preferably $C_2$–$C_4$olefins. Examples are propene, 1-butene and, in particular ethylene. The diene can contain from 5 to 12 carbon atoms, preferably from 5 to 8 carbon atoms, and can be an open-chain, cyclic or polycyclic diene. The two olefin groups of the diene are preferably connected by one or two $CH_2$ groups. Examples are 1,3-pentadiene, cyclopentadiene, 1,5-hexadiene, 1,4-cyclohexadiene, 1,4- or 1,5-heptadiene, 1,4- or 1,5-cycloheptadiene, 1,4- or 1,5-octadiene, 1,4- or 1,5-cyclooctadiene and norbornadiene. Y is preferably two ethylenes or one 1,5-hexadiene, 1,5-cyclooctadiene or norbornadiene.

In the formula XVI, Z is preferably Cl or Br. Examples of $E_1$ are $ClO_4^-$, $CF_3SO_3^-$, $CH_3SO_3^-$, $HSO_4^-$, $BF_4^-$, $B(phenyl)_4^-$, $PF_6^-$, $SbCl_6^-$, $AsF_6^-$ or $SbF_6^-$.

The metal complexes of the invention are prepared by methods known from the literature (see U.S. Pat. Nos. 5,371,256, 5,446,844, 5,583,241, and E. Jacobsen, A. Pfaltz, H. Yamamoto (Eds.), Comprehensive Asymmetric Catalysis I to II, Springer Verlag, Berlin, 1999, and literature cited therein).

The metal complexes of the invention are homogeneous catalysts, or catalyst precursors which can be activated under the reaction conditions, which can be used for asymmetric addition reactions onto prochiral unsaturated, organic compounds.

The metal complexes can, for example, be used for the asymmetric hydrogenation (addition of hydrogen) of prochiral compounds having carbon-carbon or carbon-heteroatom multiple bonds, in particular double bonds. Such hydrogenations using soluble homogeneous metal complexes are described, for example, in Pure and Appl. Chem., Vol. 68, No. 1, pp. 131–138 (1996). Preference is given to hydrogenating unsaturated compounds containing the groups C=C, C=N and/or C=O. According to the invention, metal complexes of rhodium and iridium are preferably used for the hydrogenation.

The metal complexes of the invention can also be used as catalysts for the asymmetric hydroboration (addition of boron hydrides) of prochiral organic compounds having carboncarbon double bonds. Such hydroborations are described, for example, by Tamio Hayashi in E. Jacobsen, A. Pfaltz, H. Yamamoto (Eds.), Comprehensive Asymmetric Catalysis I to III, Springer Verlag, Berlin, 1999, pages 351 to 364. Suitable boron hydrides are, for example, catechol boranes. The chiral boron compounds can be used in syntheses and/or can be converted in a manner known per se into other chiral organic compounds which are valuable building blocks for the preparation of chiral intermediates or active substances. An example of such a reaction is the preparation of 3-hydroxy-tetrahydrofuran (as described in DE 19,807,330).

The metal complexes of the invention can also be used as catalysts for the asymmetric hydrosilylation (addition of silanes) of prochiral organic compounds having carbon-carbon or carbon-heteroatom double bonds. Such hdyrosilylations are described, for example, by G. Pioda and A. Togni in Tetrahedron: Asymmetry, 1998, 9, 3093, or by S. Uemura, et al. in Chem. Commun. 1996, 847. Suitable silanes are, for example, trichlorosilane and diphenylsilane. The hydrosilylation of, for example, C=O— and C=N groups is preferably carried out using metal complexes of rhodium and iridium. For the hydrosilylation of, for example, C=C groups, preference is given to using metal complexes of palladium. The chiral silyl compounds can be used in syntheses and/or can be converted in a manner known per se into other chiral organic compounds which are valuable building blocks for the preparation of chiral intermediates or active substances. Examples of such reactions are hydrolysis to form alcohols.

The metal complexes of the invention can also be used as catalysts for asymmetric allylic substitution reactions (addition of carbon nucleophiles onto allyl compounds). Such allylations are described, for example, by A. Pfaltz and M. Lautens in E. Jacobsen, A. Pfaltz, H. Yamamoto (Eds.), Comprehensive Asymmetric Catalysis I to II, Springer Verlag, Berlin, 1999, pages 833 to 884. Suitable precursors for allyl compounds are, for example, 1,3-diphenyl-3-acetoxy-1-propene or 3-acetoxy-1-cyclohexene. Metal complexes of palladium are preferably used for these reactions. The chiral allyl compounds can be used in syntheses for preparing chiral intermediates or active substances.

The metal complexes of the invention can also be used as catalysts for asymmetric amination (addition of amines onto allyl compounds) or etherification (addition of alcohols or phenols onto allyl compounds). Such aminations and etherifications are described, for example, by A. Pfaltz and M. Lautens in E. Jacobsen, A. Pfaltz, H. Yamamoto (Eds.), Comprehensive Asymmetric Catalysis I to III, Springer Verlag, Berlin, 1999, pages 833 to 884. Suitable amines are ammonia and primary and secondary amines. Suitable alcohols are phenols and aliphatic alcohols. Metal complexes of palladium are preferably used for the amination or etherification of allyl compounds. The chiral amines and ethers can be used in syntheses for preparing chiral intermediates of active substances.

The invention further provides for the use of the metal complexes of the invention as homogeneous catalysts for preparing chiral organic compounds by asymmetric addition of hydrogen, boron-hydrides or silanes onto a carbon-carbon or carbon-heteroatom multiple bond in prochiral organic compounds, or the asymmetric addition of carbon nucleophiles or amines onto allyl compounds.

A further aspect of the invention is a process for preparing chiral organic compounds by asymmetric addition of hydrogen, boron hydrides or silanes onto a carbon-carbon or carbon-heteroatom multiple bond in prochiral organic compounds or the asymmetric addition of carbon nucleophiles, alcohols or amines onto allyl compounds in the presence of a catalyst, wherein the addition reaction is carried out in the presence of catalytic amounts of at least one metal complex of the invention.

Prochiral, unsaturated compounds preferred for hydrogenation may contain one or more, identical or different C=C, C=N and/or C=O groups in open-chain or cyclic organic compounds, with the C=C, C=N and/or C=O groups being able to be part of a ring system or exocyclic groups. The prochiral unsaturated compounds can be alkenes, cycloalkenes, heterocycloalkenes or open-chain or cyclic ketones, ketimines or ketone hydrazones. They can, for example, have the formula XVIII, $$R_7R_8C{=}D \qquad (XVIII),$$

where $R_7$ and $R_8$ are chosen so that the compound is prochiral and are each, independently of one another, an open-chain or cyclic hydrocarbon radical or heterohydrocarbon radical containing heteroatoms selected from the group consisting of O, S and N, and $R_7$ and $R_8$ each contain from 1 to 30, preferably from 1 to 20, carbon atoms;

D is O or a radical of the formula $CR_9R_{10}$ or $NR_{11}$;

$R_9$ and $R_{10}$ are, independently of one another, as defined for $R_7$ and $R_8$, $R_{11}$ is hydrogen, $C_1$–$C_{12}$alkyl, $C_1$–$C_{12}$alkoxy, $C_3$–$C_{12}$cycloalkyl, $C_3$–$C_{12}$cycloalky-$C_1$–$C_6$alkyl, $C_3–C_{11}$heterocycloalkyl, $C_3–C_{11}$heterocycloalkyl-$C_1–C_6$alkyl, $C_6–C_{14}$aryl, $C_5–C_{13}$heteroaryl, $C_7–C_{16}$-aralkyl or $C_6–C_{14}$heteroaralkyl, $R_7$ and $R_8$ together with the carbon atom to which they are bound may form a hydrocarbon ring or heterohydrocarbon ring having from 3 to 12 ring atoms;

$R_7$ and $R_9$ together with the C=C-group to which they are bound may form a hydrocarbon ring or heterohydrocarbon ring having from 3 to 12 ring atoms;

$R_7$ and $R_{11}$ together with the C=N group to which they are bound may form a hydrocarbon ring or heterohydrocarbon ring having from 3 to 12 ring atoms;

the heteroatoms in the heterocyclic rings are selected from the group consisting of O, S and N;

and $R_7$, $R_8$, $R_9$, $R_{10}$ and $R_{11}$ are unsubstituted or substituted by $C_1–C_6$alkyl, $C_1–C_6$alkoxy, cyclohexyl, $C_6–C_{10}$aryl, $C_7–C_{12}$aralkyl, $C_1–C_4$alkyl-$C_6–C_{10}$aryl, $C_1–C_4$alkoxy-$C_6–C_{10}$aryl, $C_1–C_4$alkyl-$C_7–C_{12}$aralkyl, $C_1–C_4$alkoxy-$C_7–C_{12}$aralkyl, —OH, =O, —CO—$OR_{12}$, —CO—$NR_{13}R_{14}$ or —$NR_{13}R_{14}$, where $R_{12}$ is H, an alkali metal, $C_1–C_6$alkyl, cyclohexyl, phenyl or benzyl, and $R_{13}$ and $R_{14}$ are each, independently of one another, hydrogen, $C_1–C_6$alkyl, cyclohexyl, phenyl or benzyl, or $R_{13}$ and $R_{14}$ are together tetramethylene, pentamethylene or 3-oxapentylene.

Examples of and preferences for substituents have been mentioned above.

$R_7$ and $R_8$ can each be, for example, $C_1–C_{20}$alkyl, preferably $C_1–C_{12}$alkyl, $C_1–C_{20}$heteroalkyl, preferably $C_1–C_{12}$heteroalkyl, containing heteroatoms selected from the group consisting of O, S and N, $C_3–C_{12}$-cycloalkyl, preferably $C_4–C_8$-cycloalkyl, C-bonded $C_3–C_{11}$-heterocycloalkyl, preferably $C_4–C_8$-heterocycloalkyl, containing heteroatoms selected from the group consisting of O, S and N, $C_3–C_{12}$cycloalkyl-$C_1–C_6$alkyl, preferably $C_4–C_8$cycloalkyl-$C_1–C_6$alkyl, $C_3–C_{11}$heterocycloalkyl-$C_1–C_6$alkyl, preferably $C_4–C_8$heterocycloalkyl-$C_1–C_6$alkyl, containing heteroatoms selected from the group consisting of O, S and N, $C_6–C_{14}$aryl, preferably $C_6–C_{10}$aryl, $C_5–C_{13}$heteroaryl, preferably $C_5–C_9$heteroaryl, containing heteroatoms selected from the group consisting of O, S and N, $C_7–C_{15}$aralkyl, preferably $C_7C_{11}$aralkyl, $C_6–C_{12}$heteroaralkyl, preferably $C_6–C_{10}$heteroaralkyl, containing heteroatoms selected from the group consisting of O, S and N.

If $R_7$ and $R_8$, $R_7$ and $R_9$, or $R_7$ and $R_{11}$ in each case together with the group to which they are bound form a hydrocarbon ring or heterohydrocarbon ring, the ring preferably contains from 4 to 8 ring atoms. The heterohydrocarbon ring may contain, for example, from 1 to 3 heteroatoms, preferably one or two heteroatoms.

$R_{11}$ is preferably hydrogen, $C_1–C_6$alkyl, $C_1–C_6$alkoxy, $C_4–C_8$cycloalkyl, $C_4–C_8$cycloalkyl-$C_1–C_4$alkyl, $C_4–C_{10}$heterocycloalkyl, $C_4–C_{10}$heterocycloalkyl-$C_1–C_4$alkyl, $C_6–C_{10}$aryl, $C_5–C_9$heteroaryl, $C_7–C_{12}$aralkyl and $C_5–C_{13}$heteroaralkyl.

Some examples of unsaturated organic compounds are acetophenone, 4-methoxyacetophenone, 4-trifluoromethylacetophenone, 4-nitroacetophenone, 2-chloroacetophenone, corresponding unsubstituted or N-substituted acetophenonebenzylimines, unsubstituted or substituted benzocyclohexanone or benzocyclopentanone and corresponding imines, imines selected from the group consisting of unsubstituted or substituted tetrahydroquinoline, tetrahyropyridine and dihydropyrrole, and unsaturated carboxylic acids, esters, amides and salts, for example α- and, if desired, β-substituted acrylic acids or crotonic acids. Preferred carboxylic acids are those of the formula

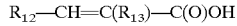

$R_{12}$—CH=C($R_{13}$)—C(O)OH and their salts, esters and amides, where $R_{12}$ is $C_1–C_6$alkyl, unsubstituted $C_3–C_8$cycloalkyl or $C_3–C_8$cycloalkyl substituted by from 1 to 4 $C_1–C_6$alkyl, $C_1–C_6$alkoxy, $C_1–C_6$alkoxy-$C_1–C_4$alkoxy groups, or $C_6–C_{10}$aryl, preferably phenyl, which may be unsubstituted or substituted by from 1 to 4 $C_1–C_6$alkyl, $C_1–C_6$alkoxy or $C_1–C_6$alkoxy-$C_1–C_4$alkoxy groups, and $R_{13}$ is linear or branched $C_1–C_6$alkyl (for example isopropyl), cyclopentyl, cyclohexyl or phenyl which may be unsubstituted or substituted as defined above, or protected amino (for example acetylamino).

The process of the present invention can be carried out at low temperatures or elevated temperatures, for example temperatures from −20 to 150° C., preferably from −10 to 100° C., particularly preferably from 10 to 80° C. The optical yields are generally better at lower temperatures than at higher temperatures.

The process of the invention can be carried out at atmospheric pressure or superatmospheric pressure. The pressure can be, for example, from $10^5$ to $2 \times 10^7$ Pa (pascal). Hydrogenations are preferably carried out under superatmospheric pressure.

Catalysts are used in amounts of from 0.0001 to 10 mol %, particularly preferably from 0.001 to 10 mol %, very particularly preferably from 0.01 to 5 mol %, based on the compound to be hydrogenated.

The preparation of the ligands and catalysts and the addition reaction can be carried out in the presence or absence of an inert solvent. It is possible to use one solvent or a mixture of solvents. Suitable solvents are, for example, aliphatic, cycloaliphatic and aromatic hydrocarbons (pentane, hexane, petroleum ether, cyclohexane, methylcyclohexane, benzene, toluene, xylene), halogenated aliphatic hydrocarbons (methylene chloride, chloroform, dichloroethane and tetrachloroethane), nitriles (acetonitrile, propionitrile, benzonitrile), ethers (diethyl ether, dibutyl ether, t-butyl-methyl ether, ethylene glycol dimethyl ether, ethylene glycol diethyl ether, diethylene glycol dimethyl ether, tetrahydrofuran, dioxane, diethylene glycol monomethyl or monoethyl ether), ketones (acetone, methyl isobutyl ketone), carboxylic esters and lactones (ethyl or methyl acetate, valerolactone), N-substituted lactams (N-methylpyrrolidone), carboximides (dimethyl acetamide, dimethylformamide), acyclic ureas (dimethylimidazoline), and sulphoxides and sulphones (dimethyl sulphoxide, dimethyl sulphones, tetramethylene sulphoxide, tetramethylene sulphones) and alcohols (methanol, ethanol, propanol, butanol, ethylene glycol monomethyl ether, ethylene glycol monoethyl ether, diethylene glycol monomethyl ether) and water. The solvents can be used alone or in a mixture of at least two solvents.

The reaction can be carried out in the presence of cocatalysts, for example quaternary ammonium halides (tetrabutylammonium iodide), and/or in the presence of protic acids, for example mineral acids (see, for example, U.S. Pat. Nos. 5,371,256, 5,446,844 and 5,583,241 and EP-A-0 691 949). Cocatalysts are particularly useful for hydrogenation.

The metal complexes used as catalysts can be added as separately prepared, isolated compounds, or they can be formed in situ prior to the reaction and then mixed with the substrate to be hydrogenated. It may be advantageous to add additional ligands in the case of the reaction using isolated metal complexes, or to use an excess of ligands in the in-situ preparation. The excess can be, for example, from 1 to 10 mol, preferably from 1 to 5 mol, based on the amount of metal compound used for the preparation.

The process of the invention is generally carried out by placing the catalyst in a reaction vessel and then adding the substrate, any desired reaction auxiliaries and the compound to be added on and subsequently starting the reaction. Gaseous compounds to be added on, for example hydrogen or ammonia, are preferably injected under pressure. The process can be carried out continuously or batchwise in various types of reactor.

The chiral organic compounds which can be prepared according to the invention are active substances or intermediates for the preparation of such substances, particularly in the field of production of pharmaceuticals and agrochemicals. Thus, for example, o,o-dialkylaryl-ketamine derivatives, in particular those having alkyl and/or alkoxy-alkyl groups, act as fungicides and especially as herbicides. Derivatives can be amine salts, acid amides, e.g. of chloroacetic acid, tertiary amines and ammonium salts (see, for example, EP-A-0 077 755 and EP-A-0 115 470).

The following examples illustrate the invention.
A) Preparation of Intermediates

EXAMPLE A1

($R_C$, $R_P$)-2-(2-bromophenyl)-1-[1-N,N-dimethylamino)ethyl]ferrocene, L2

33 ml (43 mmol) of a 1.3 molar solution of s-butyllithium in cyclohexane are added dropwise at 0° C. to a degassed solution of 10 g (38.9 mmol) of (+)-(R)-1-N,N-dimethylaminoethylferrocene (L1) in 32 ml of tetrahydrofuran (THF). After 30 minutes, likewise at 0° C., 44 ml of a 1 molar solution of $ZnCl_2$ in diethyl ether are added dropwise. The reaction mixture is subsequently stirred at room temperature for one hour. After addition of 1.4 g (2 mmol) of bis(diphenylphosphine)palladium(II) chloride and a solution of 22.64 g (80 mmol) of 2-bromo-1-iodobenzene in 50 ml of THF, the reaction mixture is refluxed for 3 days. The solvent is removed on a rotary evaporator, the residue is taken up in $CH_2Cl_2$ and extracted with water. The aqueous phase is extracted 3 times with 30 ml each time of $CH_2Cl_2$ and the combined organic phases are washed twice with 20 ml each time of water. After drying over $MgSO_4$ and removal of the solvent under reduced pressure, the residue is chromatographed on aluminium oxide 90. As eluant, use is made of a mixture of petroleum ether, ether and triethylamine in a ratio of 60:1:3. The yield is 4.65 g (11.3 mmol, 30%).

$^1$H-NMR: δ 1.61 (d, J=7.0 Hz, 3H), 1.75 (s, 6H). 3.54 (q, J=7.0 Hz, 1H), 4.13 (s, 5H, Cp), 4.23–4.25 (m, 1H, Cp), 4.32–4.34 (m, 1H, Cp), 4.59–4.61 (m, 1H, Cp), 7.07–7.11 (m, 1H, ph), 7.30–7.35 (m, 1H, ph), 7.51–7.53 (m, 1H, ph), 7.85–7.87 (m, 1H, ph). [α]$^{20}$(nm): +75.9° (589), +61.4° (578), –45.4° (546) (c=1, CHCl$_3$)

EXAMPLE A2

($R_C$,$R_P$)-1-[1-(N,N-Dimethylamino)ethyl]-2-(2-diphenylphosphinophenyl)ferrocene, L3

4.5 ml of a 1.3 molar solution of s-butyllithium in cyclohexane are slowly added dropwise at –40° C. to a degassed solution of 2 g (4.87 mmol) of L2 in 25 ml of THF. After 40 minutes, the reaction mixture is allowed to warm to room temperature, and 1.1 ml (6.6 mmol) of diphenylchlorophosphine are then added dropwise. After 18 hours, 30 ml of saturated NaHCO$_3$ solution are added. The organic phase is separated off and the aqueous phase is extracted twice with 20 ml each time of $CH_2Cl_2$. The combined organic phases are washed twice with 20 ml each time of water and dried over MgSO$_4$. Removal of the solvent under reduced pressure and chromatography on silica gel 60 (petroleum ether/diethylamine=95:5) gives 2.15 g (4.16 mmol, 85.4%) of the product.

$^1$H-NMR: δ 1.64 (d, J=7.0 Hz, 3H), 1.86 (s, 6H), 3.72 (q, J=7.0 Hz, 1H), 4.04–4.06 (m, 1H, Cp), 4.08 (s, 5H, Cp), 4.22 (m, 1H, Cp), 4.25 (m, 1H, Cp), 6.93–6.98 (m, 2H, ph), 6.99–7.02 (m, 1H, ph), 7.15–7.20 (m, 4H, ph), 7.31–7.40 (m, 6H, ph), 7.94–7.98 (m, 1H, ph). $^{31}$P-NMR: δ–14.09. [α]$^{20}$ (nm): –23.7° (589), –47.5° (578), –203.2° (546) (c=1, CHCl$_3$).

EXAMPLE A3

($R_C$,$R_P$)-1-[1-(N,N-Dimethylamino)ethyl]-2-(2-diphenylphosphinylphenyl)ferrocene, L4

0.8 ml of 30% $H_2O_2$ is added to a solution of 1 g (1.93 mmol) of L3 in 15 ml of acetone. The solution is stirred at room temperature for 45 minutes and 20 ml of saturated $Na_2S_2O_5$ solution are subsequently added. After extraction with 3×25 ml of $CH_2Cl_2$, the combined organic phases are washed with 2×20 ml of water and dried over MgSO$_4$. The solvent is removed under reduced pressure and the product is purified by chromatography on aluminium oxide 90. Nonpolar impurities are removed by elution with a mixture of petroleum ether and ethyl acetate in a ratio of 80:20, and the product is subsequently eluted with methanol. This gives 990 mg (1.86 mmol, 96%) of the product.

$^1$H-NMR: δ 1.67 (d, J=7.0 Hz, 3H), 2.03 (s, 6H), 4.04 (s, 5H, Cp), 4.04 (q, J=7.0 Hz, 1H), 4.09–4.11 (m, 1H, Cp), 4.21–4.23 (m, 1H, Cp), 4.26 (m, 1H, Cp), 7.05–7.11 (m, 1H, ph), 7.18–7.23 (m, 1H, ph), 7.28–7.33 (m, 2H, ph), 7.34–7.43 (m, 3H, ph), 7.48–7.60 (m, 4H, ph), 7.65–7.71 (m, 2H, ph), 8.10–8.13 (m, 1H, ph). $^{31}$P-NMR: δ 31.67. [α]$^{20}$ (nm): –160° (589), –200.6° (578), –449.4° (546) (c=0.5, CHCl$_3$).

EXAMPLE A4

($R_C$,$R_P$)-1-[1-(Diphenylphosphino)ethyl]-2-(2-diphenylphosphinylphenyl)ferrocene, L5

0.72 ml (4 mmol) of diphenylphosphine is added dropwise to a degassed solution of 1.2 g (2.25 mmol) of L4 in 15 ml of freshly distilled acetic acid. The reaction mixture is subsequently stirred at 100° C. for 18 hours. The solvent is removed under reduced pressure, the residue is dissolved in a little $CH_2Cl_2$ and chromatographed on aluminium oxide 90. Nonpolar impurities are removed by elution with hexane, and subsequent elution with a mixture of $CH_2Cl_2$ and methanol in a ratio of 99:1 gives 1.33 g (1.97 mmol, 89.8%) of the product. Two diastereomers are formed in a ratio of 10:1 (determined by $^{31}$P-NMR), but these are not separated. The $^1$H-NMR data are those of the main isomers.

$^1$H-NMR: δ 1.40 (dd, $J_1$=$J_2$=7.0 Hz, 3H), 3.67 (m, 1H, Cp), 3.73 (q, J=7.0 Hz, 1H) 3.80 (t, J=2.5 Hz, 1H, Cp), 4.03 (s, 5H, Cp), 5.15 (m, 1H, Cp), 7.13–7.31 (m, 13H, ph), 7.37–7.48 (m, 4H, ph), 7.49–7.59 (m, 4H, ph), 7.65–7.70 (m, 2H, ph), 8.28–8.31 (m, 1H, ph). $^{31}$P-NMR: main amount: δ 4.25, 31.38; secondary amount: δ 3.41, 29.91.

EXAMPLE A5

($R_C$,$R_P$)-1-{1-[Bis(bis-3,5-trifuoromethylphenyl) phosphino]ethyl}-2-(2-diphenylphosphinylphenyl) ferrocene, L6

1.6 g (3.5 mmol) of bis-(3,5-trifluoromethylphenyl) phosphine are added to a degassed solution of 1.25 g (2.35 mmol) of L4 in 15 ml of freshly distilled acetic acid. The reaction mixture is subsequently stirred at 100° C. for 3 days. The solvent is removed under reduced pressure, the residue is dissolved in a little $CH_2Cl_2$ and chromatographed on aluminium oxide 90. Nonpolar impurities are removed by elution with hexane, and subsequent elution with a mixture of $CH_2Cl_2$ and methanol in a ratio of 99:1 gives 2.09 g (2.21 mmol, 88.9%) of the product. Two diastereomers are formed in a ratio of 6:1 (determined by $^{31}P$-NMR), but these are not separated. The $^1H$-NMR data are those of the main isomers.

$^1H$-NMR: δ 1.32 (dd, $J_1$=6.1 Hz, $J_2$=6.8 Hz, 3H), 3.47 (m, 1H, Cp), 3.79 (dq, $J_1$=2.8 Hz, $J_2$=7.1 Hz, 1H), 3.96 (t, J=2.8 Hz, Cp), 4.08 (s, 5H, Cp), 5.03 (m, 1H, Cp), 7.1–7.15 (m, 2H, ph), 7.20–7.30 (m, 3H, ph), 7.42–7.53 (m, 3H, ph), 7.56–7.75 (m, 8H, ph), 7.86 (s, 2H, ph), 8.24–8.28 (m, 1H, ph). $^{31}P$-NMR: main components: δ 4.63, 30.29; secondary amount: δ 4.77, 29.67

EXAMPLE A6

2-(2-Bromophenyl)-1-(N,N-dimethylaminomethyl) ferrocene, L7

46 ml (60 mmol) of a 1.3 molar solution of s-butyllithium in cyclohexane are added dropwise to a degassed solution of 12 g (49.4 mmol) of N,N-dimethylaminomethylferrocene in 40 ml of THF while cooling in ice. The solution is stirred at 0° C. for 30 minutes, and 74 ml of a 1 molar solution of $ZnCl_2$ in diethyl ether are subsequently added dropwise, likewise at 0° C. The reaction mixture is stirred at room temperature for 1 hour, after which 3.5 g (5 mmol) of bis(diphenylphosphine)palladium(II) chloride and a solution of 28.3 g (100 mmol) of 2-bromoiodobenzene in 50 ml of THF are added and the mixture is refluxed for 3 days. The solvent is taken off on a rotary evaporator, the residue is taken up in $CH_2Cl_2$ and extracted with water. The aqueous phase is extracted 3 times with 50 ml each time of $CH_2Cl_2$ and the combined organic phases are washed twice with 30 ml each time of water. After drying over $MgSO_4$ and removal of the solvent under reduced pressure, the residue is chromatographed on aluminium oxide. As eluant, use is made of a mixture of petroleum ether, ether and triethylamine in a ratio of 60:1:3. The yield is 6.336 g (15.92 mmol, 32%) of L7.

$^1H$-NMR: δ 1.94 (s, 6H), 3.16, 3.50 (AB, J=13.1 Hz, 2H), 4.17 (s, 5H, Cp), 4.31 (m, 1H, Cp), 4.40 (m, 1H, Cp), 4.52 (m, 1H, Cp), 7.13 (dt, $J_1$=7.8 Hz, $J_2$=1.5 Hz, 1H, ph), 7.35 (dt, $J_1$=7.6 Hz, $J_2$=1.0 Hz, 1H, ph), 7.55 (dd, $J_1$=7.8 Hz, $J_2$=1.0 Hz, 1H, ph), 7.93 (dd, $J_1$=7.6 Hz, $J_2$=1.5 Hz, 1H, ph).

EXAPMLE A7

N-{[2-(2-Bromophenyl)ferrocenyl]methyl}-N,N,N-trimethylammonium iodide, L8

2.8 ml (45 mmol) of methyl iodide are added dropwise to a solution of 6.250 g (15.7 mmol) of L7 in 20 ml of $CH_3CN$ and the mixture is stirred at room temperature for 1 hour. 250 ml of diethyl ether are subsequently added and the mixture is stirred for another 1 hour. The yellow powder is filtered off, washed with ether and dried under reduced pressure. The yield is 8.316 g (15.4 mmol), 98% of L8.

$^1H$-NMR (MeOH-$d^4$): δ 2.79 (s, 9H), 4.42 (s, 5H, Cp), 4.55, 4.63 (AB, J=13.5 Hz, 2H), 4.69 (t, J=2.5 Hz, 1H, Cp), 4.78–4.80 (m, 2H, Cp), 7.32 (dt, $J_1$=5.9 Hz, $J_2$=1.8 Hz, 1H, ph, 7.58 (dt, $J_1$=6.3 Hz, $J_2$=1.0 Hz, 1H, ph), 7.67 (dd, $J_1$=6.8 Hz, $J_2$=1.3 Hz, 1H, ph), 8.11 (dd, $J_1$=5.8 Hz, $J_2$=1.8 Hz, 1H, ph).

EXAMPLE A8

$(S_C,S_P)$- and $(S_C,R_P)$-N-{[2-(2-Bromophenyl) ferrocenyl]methyl}-2-methoxymethylpyrrolidine, L9

2.55 g (22.1 mmol) of (S)-(−)-2-methoxymethylpyrrolidine are added to a degassed solution of 8.1 g (15.0 mmol) of L8 in 80 ml of $CH_3CN$. The reaction mixture is refluxed for 20 hours. After the solution has cooled to room temperature, 50 ml of water are added and the organic phase is separated off. The aqueous phase is extracted twice with 30 ml each time of $CH_2Cl_2$ and the combined organic phases are washed twice with 25 ml each time of water and dried over $MgSO_4$. After removal of the solvent under reduced pressure, the two diastereomers are separated by chromatography on silica gel 60. As eluant, use is made of a mixture of petroleum ether and diethylamine in a ratio of 97:3. The yield is 2.796 g (6.13 mmol, 40.8%) of the first diastereomer and 2.683 g (5.88 mmol, 39.2%) of the second diastereomer.

1st diastereomer $(S_C,R_P)$-L9

$^1H$-NMR: δ 1.39–1.45 (m, 1H), 1.47–1.54 (m, 2H), 1.64–1.74 (m, 1H), 2.00–2.07 (m, 1H), 2.51–2.54 (m, 1H), 2.57–2.61 (m, 1H), 2.90–2.99 (m, 2H), 3.23 (s, 3H), 3.45, 3.80 (AB, J=13.6 Hz, 2H), 4.18 (s, 5H, Cp), 4.27 (t, J=2.5 Hz, 1H, Cp), 4.35 (m, 1H, Cp), 4.49 (m, 1H, Cp), 7.12 (dt, $J_1$=1,8 Hz, $J_2$=7.6 Hz, 1H, ph), 7.33 (dt, $J_1$=1.3 Hz, $J_2$=7.6 Hz, 1H, ph), 7.55 (dd, $J_1$=1.3 Hz, $J_2$=8.1 Hz, 1H, ph), 7.99 (dd, $J_1$=1.8 Hz, $J_2$=7.8 Hz, 1H, ph). $[\alpha]^{20}$(nm): +10.8° (589), +2.0° (578), −55.9° (546) (c=0.52, $CHCl_3$).

2nd diastereomer $(S_C,S_P)$-L9

$^1H$-NMR: δ 1.56–1.62 (m, 1H), 1.65–1.75 (m, 2H), 1.89–1.95 (m, 1H), 2.10–2.17 (m, 1H), 2.70–2.74 (m, 1H), 3.08, 4.02 (AB, 2H, J=14.4 Hz), 3.08–3.12 (m, 1H), 3.21–3.25 (m, 1H), 3.29 (s, 3H), 3.34–3.38 (m, 1H), 3.91 (t, 1H, J=2.5 Hz, Cp), 4.04 (s, 5H, Cp), 4.08 (m, 1H, Cp), 4.70 (m, 1H, Cp), 7.11–7.17 (m, 1H, ph), 7.19–7.24 (m, 3H, ph), 7.28–7.33 (m, 1H, ph), 7.35–7.46 (m, 4H, ph), 7.48–7.56 (m, 2H, ph), 7.66–7.72 (m, 2H, ph), 8.12–8.15 (m, 1H, ph). $[\alpha]^{20}$(nm): −148.9° (589), −145.5° (578), −87.2° (546) (c=0.52, $CHCl_3$).

EXAMPLE A9

$(S_C,R_P)$-N-{[(2-(2-diphenylphosphinyl)ferroceny]methyl}-2-methoxymethylpyrrolidine, L10

3 ml (4.8 mmol) of a 1.6 molar solution of N-butyllithium in hexane are added dropwise at −40° C. to a degassed solution of 2.235 g (4.78 mmol) of $(S_C,R_P)$-L9 in 10 ml of THF. After 1 hour, the solution is warmed to room temperature and 1.36 g (1.08 ml, 5.74 mmol) of chlorodiphenylphosphine oxide are added dropwise. The reaction mixture is stirred at room temperature for 16 hours and subsequently quenched with 10 ml of saturated $NaHCO_3$ solution. The organic phase is separated off and the aqueous phase is extracted twice with 20 ml each time of $CH_2Cl_2$. The combined organic phases are washed twice with 10 ml each time of water and dried over $MgSO_4$. After removal of the solvent under reduced pressure, the product is purified by chromatography on aluminium oxide 90. As eluant, use is made of a mixture of ethyl acetate and diethylamine in a ratio of 15:1. The yield is 1.915 g (3.26 mmol, 68.1%) of L10.

$^1H$-NMR: δ 1.50–1.56 (m, 1H), 1.68–1.75 (m, 2H), 1.85–1.91 (m, 1H), 2.17–2.20 (m, 1H), 2.60–2.65 (m, 1H), 2.94–3.04 (m, 3H), 3.18 (s, 3H), 3.29, 3.95 (AB, J=14.4 Hz, 2H), 3.83 (t, J=2.5 Hz, 1H, Cp), 3.95 (m, 1H, Cp), 4.96 (s,

1H, Cp), 7.14–7.21 (m, 4H, ph), 7.25–7.28 (m, 1H, ph), 7.39–7.49 (m, 5H, ph), 7.53–7.57 (m, 1H, ph), 7.66–7.71 (m, 2H, ph), 8.15–8.18 (m, 1H, ph). $^{31}$P-NMR: δ 30.87.

$[α]^{20}$(nm): –24.2° (589), +2.1° (578), +188.1° (546) (c=0.49, CHCl$_3$)

EXAMPLE A10

($S_C$,$R_P$)-N-Methyl-N-{[2-(2-diphenylphosphinyl) ferrocenyl]methyl}-2-methoxymethylpyrrolidinium iodide L11

4.26 g (1.9 ml, 30 mmol) methyl iodide are added dropwise to a solution of 1.819 g (3.1 mmol) of L10 in 5 ml of CH$_3$CN and the mixture is stirred at room temperature for 1 hour. After addition of 250 ml of ether, the mixture is stirred for another 1 hour. The product is filtered off, washed with ether and dried under reduced pressure. The yield is 1.98 g (2.71 mmol, 87.5%) of L11.

$^1$H-NMR (MeOH-d): δ 1.76–1.87 (m, 1H), 2.15–2.25 (m, 2H), 2.69 (s, 3H), 3.23–3.29 (m, 1H), 3.36 (s, 3H), 3.56–3.62 (m, 1H), 3.63 (m, 1H), 3.68–3.84 (m, 2H), 4.10–4.14 (m, 1H), 4.29 (s, 5H, Cp), 4.33–4.35 (m, 2H, Cp), 4.67, 5.03 (AB, J=13.6 Hz, 2H), 4.77 (m, 1H, Cp), 7.10–7.16 (m, 1H, ph), 7.36–7.47 (m, 3H, ph), 7.51–7.55 (m, 2H, ph), 7.61–7.70 (m, 5H, ph), 7.75–7.78 (m, 1H, ph), 7.82–7.86 (m, 1H, ph), 8.28–8.30 (m, 1H, ph). $^{31}$P-NMR (MeOH-d$^4$): δ 36.06.

EXAMPLE A11

(R)-(+)-1-(N,N-dimethylaminomethyl)-2-(2-diphenylphosphinylphenyl)ferrocene L12

A mixture of 1.87 g (2.56 mmol) of L11, 50 ml of a 40% solution of diethylamine in water and 50 ml of benzene is heated at 110° C. for 18 hours in a 250 ml autoclave. After cooling, the phases are separated and the aqueous phase is extracted twice with 30 ml each time of CH$_2$Cl$_2$. The combined organic phases are washed twice with 25 ml each time of water and dried over MgSO$_4$. After the solvent has been taken off under reduced pressure, the residue is chromatographed on aluminium oxide 90. As eluant, use is made of a mixture of ethyl acetate and diethylamine in a ratio of 15:1. The yield is 1.231 g (2.37 mmol, 92.6%) of L12.

$^1$H-NMR: δ 2.15 (s, 6H), 3.04, 3.35 (AB, J=13.4 Hz, 2H), 3.90 (t, J=2.5 Hz, 1H, Cp), 4.03 (s, 5H, Cp), 4.03 (m, 1H, Cp), 5.00 (m, 1H, Cp), 7.13–7.23 (m, 4H, ph), 7.26–7.30 (m, 1H, ph), 7.39–7.45 (m, 4H, ph), 7.46–7.56 (m, 2H, ph), 7.68–7.74 (m, 2H, ph), 8.13–8.16 (m, 1, ph). $^{31}$P-NMR: δ 30.40.

EXAMPLE A12

(R)-(+)-1-(diphenylphosphinomethyl)-2-(2-diphenylphosphinylphenyl)ferrocene L13

1 ml (5.5 mmol) of diphenylphosphine is added to a degassed solution of 1.20 g (2.31 mmol) of L12 in 10 ml of freshly distilled acetic acid and the reaction mixture is heated at 100° C. for 3 days. The solvent is taken off under reduced pressure and the residue is chromatographed on aluminium oxide 90. As eluant, use is made of a mixture of CH$_2$Cl$_2$ and methanol in a ratio of 99:1. The yield is 1.081 g (1.77 mmol, 76%) of L13.

$^1$H-NMR: δ 2.72, 2.98 (AB, J$_{AB}$=15.2 Hz, J$_{AP}$=3.3 Hz, 2H), 3.53 (m, 1H, Cp), 3.79 (t, J=2.5 Hz, 1H, Cp), 4.01 (s, 5H, Cp), 4.99 (m, 1H, Cp), 7.15–7.20 (m, 2H, ph), 7.21–7.30 (m 3H, ph), 7.34–7.49 (m, 15H, ph), 7.57–7.62 (m, 1H, ph), 7.68–7.74 (m, 2H, Cp), 8.19–8.22 (m, 1H, ph). $^{31}$P-NMR: δ –14.40, –29.81.

EXAMPLE A13

(S)-(–)-1-(N,N-dimethylaminomethyl)-2-(2-diphenylphosphinylphenyl)ferrocene, L14, and (S)-1-(diphenylphosphinylmethyl)-2-(2-diphenylphosphinylphenyl)ferrocene, L15

Reaction of (1R,2S)-O-methylephedrine with N-ferrocenylmethyl-N,N,N-trimethylammonium iodide (D. Lednicer and C. R. Hauser, J. Org. Chem., 40 (1960), 31) in acetonitrile gives the intermediate (–)-(1R,2S)-N-(ferrocenylmethyl)-N-methyl-1-methoxy-1-phenyl-prop-2-ylamine.

The preparation of (1R,2S,$S_p$)-N-[2-(2-iodophenyl) ferrocenylmethyl]-N-methyl-1-methoxy-1-phenylprop-2-ylamine from the intermediate (–)-(1R,2S)-N-(ferrocenylmethyl)-N-methyl-1-methoxy-1-phenylprop-2-ylamine is carried out as follows: 5 ml (7.1 mmol) of a 1.7 molar solution of t-butyllithium in pentane are added dropwise at –78° C. to a degassed solution of 2.67 g (7.1 mmol) of (–)-(1R,2S)-N-(ferrocenylmethyl)-N-methyl-1-methoxy-1-phenylprop-2-ylamine in 80 ml of pentane. The solution is firstly stirred for 1.5 hours at –78° C. and then for another 1.5 hours at –40° C., with an orange suspension being formed. 9.24 ml (9.2 mmol) of a 1 molar solution of ZnCl$_2$ in diethyl ether are added dropwise at –78° C. to the suspension. The reaction mixture is subsequently stirred at room temperature for 30 minutes. After addition of 0.498 g (0.7 mmol) of bis(diphenylphosphine)palladium(II) chloride and a solution of 4.02 g (14.2 mmol) of 2-bromo-1-iodobenzene in 20 ml of diethyl ether, the reaction mixture is refluxed for 2 days. 20 ml of a saturated aqueous NaHCO$_3$ solution are added, the phases are separated and the aqueous phase is extracted three times with 30 ml each time of CH$_2$Cl$_2$. The combined organic phases are washed twice with 20 ml each time of water and dried over MgSO$_4$. After removal of the solvent under reduced pressure, the residue is chromatographed on silica gel 60. As eluant, use is made of a mixture of petroleum ether, ether and triethylamine in a ratio of 10:3:1. The yield is 185 mg (0.32 mmol, 4%). The melting point is 189° C.

$^1$H-NMR: δ: 0.43 (d, J=6.8 Hz, 3H), 2.60 (dq, J=6.8 and 3.5 Hz, 1H), 3.16 (s, 3H), 3.18 (s, 3H), 3.81 (s, 5H), 4.13 (m, 1H), 4.21–4.25 (m, 3H), 4.33 (m, 1H), 6.77 (m, 1 H, CH), 7.02–7.09 (m, 4H), 7.18–7.23 (m, 3H), 7.32–7.39 (m. 2H). MS (EI, 130° C.): m/e (rel %): 579 (13, M$^+$), 472 (2), 431 (26), 430 (100). $[α]^{20}$(nm): +181.4 (589), +196.9 (578), +273.7 (546) (c=0.45, CHCl$_3$)

Using a method analogous to the above examples, (1R, 2S,$S_p$)-N-[2-(2-diphenylphosphinylphenyl) ferrocenylmethyl]-N-methyl-1-methoxy-1-phenylprop-2-ylamine can be obtained by lithiation of (1R,2S,$S_p$)-N-[2-(2-iodophenyl)ferrocenylmethyl]-N-methyl-1-methoxy-1-phenylprop-2-ylamine using sec-butyllithium, followed by reaction with P-chlorodiphenylphosphine and subsequent oxidation using hydrogen peroxide. This intermediate is converted by methods known to those skilled in the art either into (S)-1-(N,N-dimethylaminomethyl)-2-(2-diphenylphosphinylphenyl)ferrocene (by reaction with methyl iodide and subsequent substitution by dimethylamine), L14, or into (S)-1-(diphenylphosphinylmethyl)-2-(2-diphenylphosphinylphenyl)ferrocene (by reaction with diphenylphosphine in acetic acid), L15.

B) Preparation of Ligands

EXAMPLE B1

($R_C,R_P$)-1-[1-(diphenylphosphino)ethyl]-2-(2-diphenylphosphinophenyl)ferrocene, B1a 7 ml of polymethyl hydrosiloxane and 3.8 ml of Ti(Oi-propyl)$_4$ are added to a degassed solution of 1.2 g (1.78 mmol) of L5 in 20 ml of THF. The reaction mixture is refluxed for 18 hours, with the solution becoming deep violet. 15 ml of hexane are subsequently added and the mixture is refluxed for another 2 hours. The reaction mixture is, without further work-up, introduced onto an aluminium oxide column and the product is eluted using a mixture of petroleum ether, ethyl acetate and methanol in a ratio of 90:10:1. In most cases, it is necessary to repeat the chromatography a second time in order to obtain the product in pure form. The yield is 971 mg (1.48 mmol, 83%).

$^1$H-NMR: main amount: δ 1.28 (dd, $J_1=J_2=7.3$ Hz, 3H), 3.40 (q, J=7.0 Hz, 1H), 3.62 (m, 1H Cp), 3.84 (m, 1H, Cp), 3.93 (m, 1H, Cp), 4.05 (s, 5H, Cp), 6.90–6.94 (m, 1H, ph), 7.06–7.23 (m, 14H, ph), 7.25–7.36 (m, 8H, ph), 8.03–8.06 (m, 1H, ph); secondary amount: δ 0.79 (dd, $J_1=7.0$ Hz, $J_2=9.0$ Hz, 3H), 3.28 (ddd, $J_1=4.0$ Hz, $J_2=7.0$ Hz, $J_3=11.0$ Hz, 1H), 3.76–3.78 (m, 1H, Cp), 3.93 (s, 5H, Cp), 4.03 (t, J=2.5 Hz, 1H, Cp), 4.11 (m, 1H, Cp), 6.91–6.94 (m, 1H, ph), $^{31}$P-NMR: main amount: δ −13.74 (d, J=15.9 Hz), 3.77 (d, J=16.8 Hz); secondary amount: δ −14.40 (d, J=5.9 Hz), −1.82 (d, J=5.9 Hz). [α]$^{20}$(nm): main amount: +9.4° (589), 0° (578), −65.20° (546) (c=0.5, CHCl$_3$); secondary amount: +88.60° (589), +81.10° (578), +25.70° (546) (c=0.49, CHCl$_3$).

EXAMPLE B2

($R_C,R_P$)-1-{1-[Bis(bis-3,5-trifluoromethylphenyl)phosphino]ethyl}-2-(2-diphenyl-phosphinophenyl)ferrocene, B1c 9.2 ml of polymethylhydrosiloxane and 5.04 ml of Ti(Oi-propyl)$_4$ are added to a degassed solution of 1.97 g (2.08 mmol) of L6 in 20 ml of THF. The reaction mixture is refluxed for 18 hours, with the solution becoming deep violet. 15 ml of hexane are subsequently added and the mixture is refluxed for another 2 hours. The reaction mixture is, without further work-up, introduced onto an aluminium oxide column and the product is eluted using a mixture of petroleum ether, ethyl acetate and methanol in a ratio of 90:10:1. The yield is 1.78 g (1.91 mmol, 91.8%). The two diastereomers are separated by chromatography on silica gel. As eluant, use is made of a mixture of petroleum ether and CH$_2$Cl$_2$ in a ratio of 80:20.

$^1$H-NMR: δ 1.32 (dd, $J_1=6.1$ Hz, $J_2=6.8$ Hz, 3H), 3.29 (s, 1H, Cp), 3.66 (dq, $J_1=J_2=7.1$ Hz, 1H), 3.86 (m, 1H, Cp), 4.02 (t, J=2.5 Hz, 1H, Cp), 4.16 (s, 5H, Cp), 7.06–7.11 (m, 2H, ph), 7.13–7.19 (m, 3H, ph), 7.25–7.29 (m, 2H, ph), 7.38–7.50 (m, 6H, ph), 7.59 (d, J=4.0 Hz, 2H, ph), 7.80 (s, 1H, ph), 7.90 (s, 1H, ph), 7.97 (d, J=6.1 Hz, 2H, ph), 8.12–8.15 (m, 1H, ph). $^{31}$P-NMR: main component: δ −14.04 (d, J=23.5 Hz), 3.55 (d, J=23.5 Hz); secondary amount: δ −15.19 (d, J=28.5 Hz), −5.16 (d, J=28.5 Hz). [α]$_{20}$(nm): −0.88 (589), −7.72 (578), −52.8 (546) (c=0.57, CHCl$_3$).

EXAMPLE B3

(R)-(+)-1-(diphenylphosphinomethyl)-2-(2-diphenylphosphinophenyl)ferrocene, B2a 4.6 g of polymethylhydrosiloxane and 2.52 ml of Ti(i-propoxide)$_4$ are added to a degassed solution of 1.05 g (1.72 mmol) of L13 in 10 ml of THF. The reaction mixture is refluxed for 18 hours, with the solution becoming deep violet. 15 ml of hexane are subsequently added and the mixture is refluxed for another 2 hours. The reaction mixture is, without further work-up, introduced onto an aluminium oxide column and the product is eluted using a mixture of petroleum ether, ethyl acetate and methanol in a ratio of 90:10:1. In most cases, the chromatography has to be repeated a second time in order to obtain the product in pure form. The yield is 720 mg (1.21 mmol, 70%) of B2a.

$^1$H-NMR: δ 2.78, 2.87 (AB, $J_{AB}=14.9$ Hz, $J_{AP}=1.3$ Hz, 2H), 3.81 (s, 1H, Cp), 3.98 (t, J=2.5 Hz, 1H, Cp), 4.05 (m, 1H, Cp), 4.11 (s, 5H, Cp), 6.90–6.93 (m, 1H, ph), 7.04–7.10 (m, 2H, ph), 7.16–7.24 (m, 7H, ph), 7.26–7.32 (m, 9H, ph), 7.34–7.48 (m, 4H, ph), 8.04–8.07 (m, 1H, ph). $^{31}$P-NMR: δ −12.45 (d, J=6.2 Hz), −15.44 (d, J=6.2 Hz).

EXAMPLE B4

($R_C,R_P$)-1-[1-(dicyclohexylphosphino)ethyl]-2-(2-diphenylphosphinophenyl)ferrocene B1e This ligand is obtained by a method analogous to Example B1.

$^1$H-NMR: δ 0.80–1.80 (m, 22H), 1.63 (dd, $J_1=J_2=7.3$ Hz, 3H), 2.94 (q, J=7.3 Hz, 1H), 3.95 (m, 1H, Cp), 4.1 (s, 6H, Cp), 4.19 (m, 1H, Cp), 6.98–7.00 (m, 1H, ph), 7.15–7.27 (m, 6H, ph), 7.31–7.39 (m, 6H, ph), 8.03–8.06 (m, 1H, ph). $^{31}$P-NMR: δ −14.15 (d, J=16.8 Hz), 14.85 (d, J=16.8 Hz). [α]$^{20}$(nm): −8.6° (589), −21.5° (578), −107.1° (546) (c =0.5, CHCl$_3$).

EXAMPLE B5

($R_C,R_P$)-1-[1-(di-tert-butylphosphino)ethyl]-2-(2-diphenylphosphinophenyl)ferrocene, B1d This ligand is obtained by a method analogous to Example B1.

$^1$H-NMR: δ 0.85 (d, J=10.0 Hz, 9H), 1.16 (d, J=10.5 Hz, 9H), 1.89 (dd, $J_1=3.0$ Hz, $J_2=7.5$ Hz, 3H), 3.04 (q, J=7.5 Hz, 1H), 3.85–3.87 (m, 1H, Cp), 4.09 (t, J=2.2 Hz, 1H, Cp), 4.16 (s, 5H, Cp), 4.23 (m, 1H, Cp), 7.03–7.06 (m, 1H, ph), 7.13–7.19 (m, 4H, ph), 7.31–7.39 (m, 8H, ph), 8.01–8.04 (m, 1H; ph). $^{31}$P-NMR: d −14.50 (d, J=28.7 Hz), 42.88 (d, J=29.7 Hz). [α]$^{20}$(nm): −37.20° (589), −52.6° (578), −157.2° (546) (c =0.5, CHCl$_3$).

EXAMPLE B6

($R_C,R_P$)-1-{1-[Bis(3,5-dimethyl-4-methoxy)phenylphosphino]ethyl}-2-(2-diphenylphosphinophenyl)ferrocene, B1b This ligand is obtained by a method analogous to Example B1.

$^1$H-NMR: δ 1.29 (dd, $J_1=7.3$ Hz, $J_2=14.4$ Hz, 3H), 2.20 (s, 6H), 2.21 (s, 6H), 3.41 (q, J=7.3 Hz, 1H), 3.64 (m, 1H, Cp), 3.70 (s, 3H), 3.72 (s, 3H), 3.86 (m, 1H, Cp), 3.96 (t, J=2.5 Hz, Cp), 4.13 (s, 5H, Cp), 6.90 (d, $J_{PH}=6.1$ Hz, ph), 6.85–6.99 (m, 1H, ph), 7.07 (d, $J_{PH}=7.1$ Hz, ph), 7.06–7.21 (m, 6H, ph), 7.31–7.42 (m, 6H, ph), 8.09–8.12 (m, 1H, ph). $^{31}$P-NMR: δ −13.98 (d, J=15.4 Hz), 2.20 (d, J=15.4 Hz). [α]$^{20}$(nm): 21.8° (589), 17,2° (578), −24.4° (546) (c=0.5, CHCl$_3$).

EXAMPLE B7

($R_C$,$R_P$)-1-{1-[Bis(3,5-trifluoromethyl)phenylphosphino]ethyl}-2-(2-diphenylphosphinophenyl) ferrocene, B1 c This ligand is obtained by a method analogous to Example B1.

$^1$H-NMR: δ 1.32 (dd, $J_1$=6.1 Hz, $J_2$=6.8 Hz, 3H), 3.29 (s, 1H, Cp), 3.66 (dq, $J_1$=$J_2$=7.1 Hz, 1H), 3.86 (m, 1H, Cp), 4.02 (t, J=2.5 Hz, 1H, Cp), 4.16 (s, 5H, Cp), 7.06–7.11 (m, 2H, ph), 7.13–7.19 (m, 3H, ph), 7.25–7.29 (m, 2H, ph), 7.38–7.50 (m, 6H, ph), 7.59 (d, J=4.0 Hz, 2H, ph), 7.80 (s, 1H, ph), 7.90 (s, 1H, ph), 7.97 (d, J=6.1 Hz, 2H, ph), 8.12–8.15 (m, 1H, ph). $^{31}$P-NMR: δ −14.04 (d, J=23.5 Hz), 3.55 (d, J=23.5 Hz). $[α]^{20}$(nm): −0.88° (589), −7.72° (578), −52.8° (546) (c=0.57, CHCl$_3$).

EXAMPLE B8

(S)-1-(di-tert-butylphosphinomethyl)-2-(2-diphenylphosphinophenyl)ferrocene, (S)-B2b.

This ligand is obtained by a method analogous to Example B1.

$^1$H-NMR: δ 0.86 (d, J=10.9 Hz, 9H), 1.17 (d, J=10.6 Hz, 9H), 2.47, 2.64 (AB, $J_{AB}$=15.9 Hz, $J_{AP}$4.8 Hz, 2H), 3.98 (m, 1H, Cp), 4.07 (t, J=2.5 Hz, 1H, Cp), 4.12 (s, 5H, Cp), 4.52 (m, 1H, Cp), 6.97–7.00 (m, 1H, ph), 7.07–7.11 (m, 2H, ph), 7.19–7.22 (m, 4H, ph), 7.24–7.29 (m, 2H, ph), 7.33–7.38 (m, 3H, ph), 7.40–7.44 (m, 1H, ph), 8.11–8.14 (m, 1 H, ph). $^{31}$P-NMR: δ −13.54 (d, J=3,7 Hz), 30.18 (d, J=3.7 Hz). $[α]^{20}$(nm): −69.0° (589), −60.2° (578), 9° (546) (c=0.5, CHCl$_3$).

C) Preparation of Catalysts

The catalysts or catalyst precursors are prepared by known methods and are subsequently used as isolated compounds in the catalytic reactions. It is frequently advantageous to prepare the catalyst in situ immediately before the reaction.

EXAMPLE C1

Preparation of [Rh(NBD)(B1c)]BF$_4$ 4.73 mg (0.0126 mmol) of [Rh(NBD)$_2$]BF$_4$ and 11.8 mg (0.0126 mmol) of B1c are placed in a flask provided with a magnetic stirrer and are blanketed with argon by repeatedly evacuating the flask and flushing it with argon. 5 ml of degassed tetrahydrofuran are then added and the mixture is stirred for 15 minutes. Addition of 20 ml of diethyl ether produces a red precipitate which is separated off by filtration. After drying in a high vacuum, [Rh(NBD)(B1c)]BF$_4$ is isolated in a yield of 85%.

D) Use Examples

The following ligands are used:

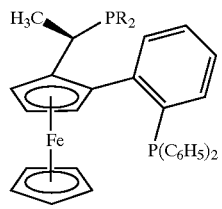

B1

B1a: R = C$_6$H$_5$ (ph)
B1b: R =3,5-CH$_3$-4-OMe—C$_6$H$_2$
B1c: R = 3,5-CF$_3$—C$_6$H$_3$
B1d: R = C(CH$_3$)$_3$ (tBu)
B1e: R = C$_6$H$_{11}$ (cy)

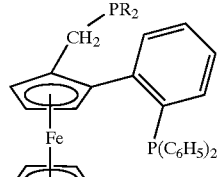

B2

B2a: R = C$_6$H$_5$
B2b: R = R═C(CH$_3$)$_3$ (tBu)

EXAMPLE D1

Preparation of dimethyl 2-methylsuccinate 4.73 mg (0.0126 mmol) of [Rh(NBD)$_2$]BF$_4$ and 8.55 mg (0.0133 mmol) of B2a are placed in a flask provided with a magnetic stirrer and blanketed with argon by repeatedly evacuating the flask and flushing it with argon. 5 ml of degassed methanol are then added and the mixture is stirred for 15 minutes. 0.4 g (2.53 mmol) of dimethyl itaconate and 5 ml of degassed methanol are subsequently introduced into a 10 ml Schlenk flask filled with an argon atmosphere. Stirring is continued until a homogeneous solution is formed. The solution is injected by means of a steel capillary into a 180 ml glass reactor filled with argon. Finally, 1.05 bar of hydrogen are introduced in three flushing cycles (argon 1 bar/hydrogen 1 bar). The hydrogenation is started by switching on the stirrer and is carried out at 25° C. The course of the reaction is followed via the hydrogen consumption (pressure decrease in the hydrogen reservoir). After a reaction time of 20 hours, the conversion is found to be complete. The enantiomeric purity of dimethyl 2-methyl succinate is 94.6% of (R).

EXAMPLE D2

Preparation of the methyl ester of N-acetylphenylalanine

The procedure of Example D1 is repeated, but 0.52 g (2.37 mmol) of methyl cis-2-ace-tamidocinnamate is hydrogenated. After 20 hours the conversion is found to be complete. The enantiomeric purity of the methyl ester of N-acetylphenylalanine is 94% of (R).

EXAMPLE D3

Preparation of 2-methyl-3-phenylpropionic acid 4.73 mg (0.0126 mmol) of [Rh(NBD)$_2$]BF$_4$ and 12.2 mg (0.0131 mmol) of B1c are placed in a flask provided with a magnetic stirrer and blanketed with argon by repeatedly evacuating the flask and flushing it with argon. 5 ml of degassed methanol are then added and the mixture is stirred for 15 minutes. 0.405 g (2.497 mmol) of 2-methylcinnamic acid and 5 ml of degassed methanol are subsequently introduced into a 10 ml Schlenk flask filled with an argon atmosphere. Stirring is continued until a homogeneous solution is formed. The solution is injected by means of a steel capillary into a 50 ml steel autoclave filled with argon. Finally, 5 bar of hydrogen are introduced in three flushing cycles (argon 20 bar/hydrogen 20 bar). The hydrogenation is started by switching on the stirrer and is carried out at 25° C. The course of the reaction is followed via the hydrogen consumption (pressure decrease in the hydrogen reservoir). After a reaction time of 20 hours, the conversion is found to be complete. The enantiomeric purity of 2-methyl-3-phenylpropionic acid is 81.7% of (R).

EXAMPLE D4

Preparation of the methyl ester of N-acetylphenylalanine

The procedure of Example D1 is repeated, but 0.52 g (2.37 mmol) of methyl cis-2-acetamidocinnamate is hydrogenated. 10 mg (0.131 mmol) of B1b are used. After 20 hours, the conversion is found to be complete. The enantiomeric purity of the methyl ester of N-acetylphenylalanine is 95.3% of (R).

EXAMPLE D5

Preparation of 2,3-diphenylpropionic acid 4.73 mg (0.0126 mmol) of $[Rh(NBD)_2]BF_4$ and 8.8 mg (0.0136 mmol) of B1d are placed in a flask provided with a magnetic stirrer and blanketed with argon by repeated evacuating the flask and flushing it with argon. 5 ml of degassed methanol are then added and the mixture is stirred for 15 minutes. 0.405 g (2.497 mmol) of trans-2-phenylcinnamic acid and 5 ml of degassed methanol are subsequently introduced into a 10 ml Schlenk flask filled with an argon atmosphere. Stirring is continued until a homogeneous solution is formed. The solution is injected by means of a steel capillary into a 50 ml steel autoclave filled with argon. Finally, 6 bar of hydrogen are introduced in three flushing cycles (argon 20 bar/hydrogen 20 bar). The hydrogenation is started by switching on the stirrer and is carried out at 25° C. The course of the reaction is followed via the hydrogen consumption (pressure decrease in the hydrogen reservoir). After a reaction time of 20 hours, the conversion is found to be complete. The enantiomeric purity of 2,3-diphenylpropionic acid is 65.3%.

EXAMPLE D6

Preparation of ethyl lactate 2.9 mg (0.0063 mmol) of $[Rh(NBD)Cl]_2$ and 9.4 mg (0.0135 mmol) of B1e are placed in a flask provided with a magnetic stirrer and blanketed with argon by repeatedly evacuating the flask and flushing it with argon. 5 ml of degassed toluene are then added and the mixture is stirred for 15 minutes. 0.294 g (2.532 mmol) of ethyl pyruvate and 5 ml of degassed toluene are subsequently introduced into a 10 ml Schlenk flask filled with an argon atmosphere. Stirring is continued until a homogeneous solution is formed. The solution is injected by means of a steel capillary into a 50 ml steel autoclave filled with argon. Finally, 80 bar of hydrogen are introduced in three flushing cycles (argon 20 bar/hydrogen 20 bar). The hydrogenation is started by switching on the stirrer and is carried out at 25° C. The course of the reaction is followed via the hydrogen consumption (pressure decrease in the hydrogen reservoir). After a reaction time of 16 hours, the conversion is found to be >98.5%. The enantiomeric purity of ethyl lactate is 62.9% of (R).

EXAMPLE D7

Preparation of 1,3-diphenyl-3-(2'-dimethyl malonato))-1-propene 252 mg of trans-1,3-diphenylprop-3-en-1-yl acetate (1 mmol), 396 mg of dimethyl malonate (340 µl, 3 mmol), 610 mg of succinic anhydride (741 µl, 3 mmol) and a catalytic amount of potassium acetate are added to a degassed solution of 1.8 mg (0.005 mmol) of $[Pd(\eta^3-C_3H_5)Cl]_2$ and 0.01 mmol of B1a in 1 ml of $CH_2Cl_2$. The reaction mixture is stirred at room temperature. The course of the reaction is followed by means of thin layer chromatography (silica gel, petroleum ether/ethyl acetate=95/5) After 18 hours, 15 ml of diethyl ether are added, the organic phase is separated off and washed twice with saturated aqueous $NH_4Cl$ solution. After drying over $Na_2SO_4$, the solvent is removed on a rotary evaporator and the residue is chromatographed (silica gel 60, petroleum ether/$CH_2Cl_2$=50/50, detection at 280 nm). The enantiomeric purity of the product is 76.6% of (S) (determined by means of HPLC: Chiralcel OD, 2-propanol/hexane=2/98, 0.5 ml/min). The absolute configuration of the product is determined by means of the optical rotation.

EXAMPLE D8

Preparation of 1,3-diphenyl-3-benyzlamino-1-propene

A solution of 252 mg (1 mmol) of trans-1,3-diphenylprop-3-en-1-yl acetate, 0.01 mmol of B2b and 1.8 mg (0.005 mmol) of $[Pd(\eta^3-C_3H_5)Cl]_2$ is degassed and stirred at room temperature for 15 minutes. After addition of 321 mg (3 mmol) of benzylamine and a catalytic amount of potassium acetate, the reaction mixture is stirred at room temperature for 18 hours, with the course of the reaction being able to be followed by means of thin layer chromatography (silica gel 60, PE/EE=95:5). After removal of the solvent at reduced pressure, the residue is chromatographed on silica gel 60. As eluant, use is made of a mixture of petroleum ether and ethyl acetate in a ratio of 90:10, and detection is carried out at 280 nm. The enantiomeric purity is determined by means of HPLC on a chiral column (Chiralcel OD-H, 0.2% diethylamine, 0.25% of isopropanol in hexane) and is 90.7% of (R). (The absolute configuration is determined from the optical rotation).

EXAMPLE D9

Preparation of 4-methoxylphenyl-1'-ethanol

A solution of 4 mg (0.01 mmol) of $Rh(COD)_2BF_4$ and 0.01 mmol of B1d in 1 ml of degassed THF is stirred for 15 minutes. 134 mg (135 µl, 1 mmol) of 4-methoxy-styrene and 1.05 ml (1.05 mmol) of a 1M solution of catecholborane in THF are subsequently added slowly and the reaction mixture is stirred for another 15 minutes.

2 ml of methanol, 2.4 ml of 3N NaOH and 0.25 ml of 20% $H_2O_2$ are added while cooling in ice. The solution is stirred at room temperature for another 3 hours. After extraction with 3×20 ml of diethyl ether, the combined organic phases are washed twice with 20 ml each time of 1N NaOH and once with 10 ml of saturated aqueous NH$_4$Cl solution. After drying over MgSO$_4$, the solvent is taken off on a rotary evaporator. The residue is purified by means of bulb tube distillation (160° C., 20 torr).

The ratio of regioisomers is determined by means of GC (HP-Ultra 1 100% crosslinked (25 m×0.32 mm×52 µm), column temperature: 145° C., concentration of the sample: 2 mg/ml, injection volume: 1 µl). The ratio of linear/branched is 84:16.

The enantiomeric purity of the 4-methoxyphenyl-1'-ethanol isolated was determined by means of HPLC (Chiralcel OD, 25° C., 10% 2-propanol/hexane, 0.5 ml/min); and is 64% of (R).

(The absolute configuration is determined from the optical rotation).

What is claimed is:

1. A compound of the formula I or Ia in the form of a racemate, a mixture of diastereomers or in essentially enantiomerically pure form,

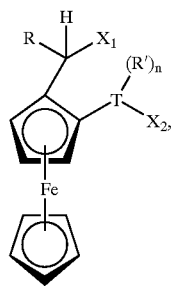
(I)

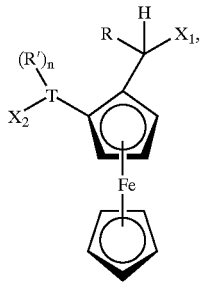
(Ia)

where

R is hydrogen, C$_1$–C$_8$alkyl, C$_5$–C$_{12}$cycloalkyl, phenyl or phenyl substituted by from 1to 3 C$_1$–C$_4$alkyl or C$_1$–C$_4$alkoxy groups;

n is 0 or an integer from 1 to 4 and R' are identical or different substituents selected from the group consisting of C$_1$–C$_4$alkyl, C$_1$–C$_4$fluoroalkyl and C$_1$–C$_4$alkoxy;

X$_1$ and X$_2$ are each, independently of one another, secondary phosphino;

T is C$_6$–C$_{20}$arylene or C$_3$–C$_{16}$heteroarylene;

and X$_2$ is bound in the ortho position relative to the T-cyclopentadienyl bond.

2. A compound of the formula Ib or Ic according to claim 1 in the form of a racemate, a mixture of diastereomers or in essentially enantiomerically pure form,

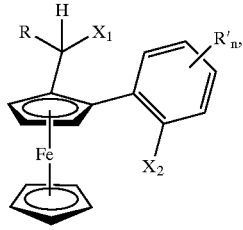
(Ib)

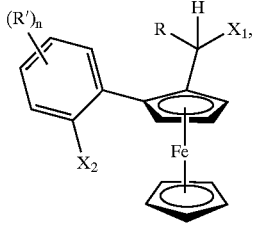
(Ic)

where

R is hydrogen, C$_1$–C$_8$ alkyl, C$_5$–C$_{12}$cycloalkyl, phenyl or phenyl substituted by from 1 to 3 C$_1$–C$_4$alkyl or C$_1$–C$_4$alkoxy groups;

n is 0 or an integer from 1 to 4 and R' are identical or different substituents selected from the group consisting of C$_1$–C$_4$alkyl, C$_1$–C$_4$fluoroalkyl and C$_1$–C$_4$-alkoxy, or two substituents R' form the group —CH=CH—CH=CH— which may be unsubstituted or substituted by C$_1$C$_4$alkyl or C$_1$–C$_4$alkoxy; and X$_1$ and X$_2$ are each, independently of one another secondary phosphino.

3. A compound according to claim 1, wherein R is hydrogen, C$_1$–C$_4$alkyl, cyclopentyl, cyclohexyl or phenyl.

4. A compound according to claim 1, which has the formula Id or Ie,

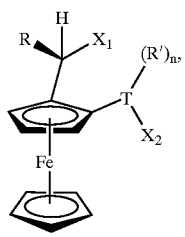
(Id)

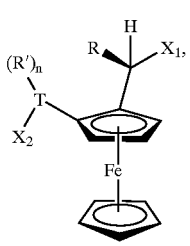
(Ie)

where R is C$_1$C$_8$ alkyl, C$_5$–C$_{12}$cycloalkyl, phenyl or phenyl substituted by from 1 to 3 C$_1$–C$_4$alkyl or C$_1$–C$_4$alkoxy groups, and T, R', n, X$_1$ and X$_2$ are as defined in claim 1.

5. A compound according to claim 1, wherein n is 0, 1 or 2.

6. A compound according to claim 1, wherein the phosphine groups X$_1$ and X$_2$ contain two identical or two different hydrocarbon radicals containing from 1 to 22 carbon atoms, or the phosphine groups are each a 3- to 8-membered phosphanyl radical.

7. A compound as claimed in claim 6, wherein the phosphine groups contain two identical or different radicals selected from the group consisting of linear or branched $C_1$–$C_{12}$alkyl; unsubstituted or $C_1$–$C_6$alkyl- or $C_1$–$C_6$alkoxy-substituted $C_5$–$C_{12}$cycloalkyl or $C_5$–$C_{12}$cycloalkyl-$CH_2$—; phenyl or benzyl; or phenyl or benzyl substituted by halogen, $C_1$–$C_6$alkyl, $C_1$–$C_6$haloalkyl, $C_1$–$C_6$alkoxy, $C_1$–$C_6$haloalkoxy, $(C_6H_5)_3Si$, $(C_1$–$C_{12}$alkyl$)_3Si$, secondary amino or —$CO_2$—$C_1$–$C_6$alkyl, or the phosphine groups are each a 3- to 6-membered, unsubstituted or halogen-, $C_1$–$C_6$alkyl- or $C_1$–$C_6$alkoxy-substituted phosphanyl radical.

8. A compound according to claim 1, wherein $X_1$ is the group —$PR_1R_2$ and $X_2$ is the group —$PR_3R_4$, where $R_1$, $R_2$, $R_3$ and $R_4$ are each, independently of one another, a hydrocarbon radical which has from 1 to 20 carbon atoms and is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3Si$, $(C_1$–$C_{12}$-alkyl$)_3Si$, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

9. A compound according to claim 1 which has the formula

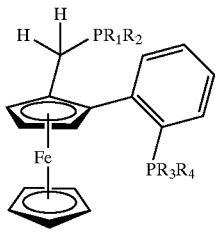

(Ih)

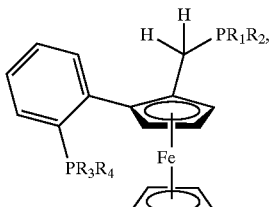

(Ii)

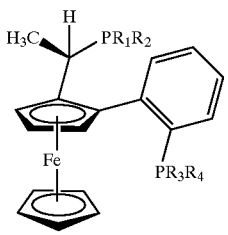

(Ij)

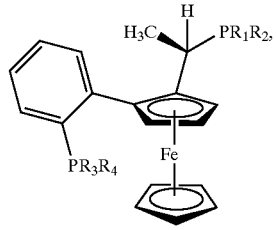

(Ik)

where $R_1$, $R_2$, $R_3$ and $R_4$ are identical or different and are selected from the group consisting of α-branched $C_3$–$C_6$alkyl, unsubstituted $C_5$–$C_7$cycloalkyl and $C_5$–$C_7$cycloalkyl substituted by from one to three $C_1$–$C_4$alkyl or $C_1$–$C_4$alkoxy groups and unsubstituted phenyl and phenyl substituted by from one to three $C_1$–$C_4$alkyl, $C_1$–$C_4$alkoxy and $C_1$–$C_4$fluoroalkyl groups and unsubstituted and $C_1$–$C_4$alkyl- or $C_1$–$C_4$alkoxy-substituted dimethylene, trimethylene, tetramethylene and hexamethylene.

10. A process for preparing a compound of the formula I according to claim 1, wherein
a) a compound of the formula II

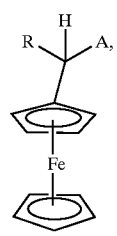

(II)

where R is as defined in claim 1 and A is secondary amino, is firstly reacted with a lithium alkyl, the reaction mixture is treated with a zinc dihalide, and is then reacted in the presence of Pd(0) or Pd(II) complexes as catalyst with a compound of the formula

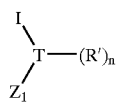

where R', T and n are as defined in claim 1 and $Z_1$ is F, Cl, Br or I, to form a compound of the formula III,

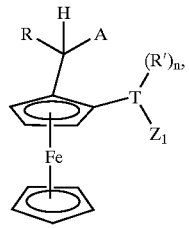

(III)

b) the compound of the formula III is reacted firstly with a lithium alkyl and then with a secondary halophosphine $X_2Cl$ or $X_2Br$ to form a compound of the formula IV, where $X_2$ is as defined in claim 1,

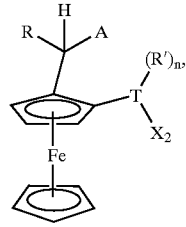
(IV)

c) the phosphine group of the compound of the formula IV is oxidised to form a compound of the formula V,

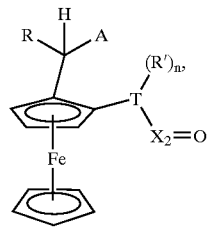
(V)

d) the oxidised compound of the formula V is reacted in the presence of an acid with a secondary phosphine $X_1H$, where $X_1$ is as defined in claim 1, to form a compound of the formula VI,

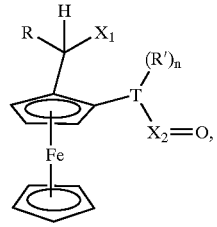
(VI)

e) the $X_2$=O group in the compound of the formula VI is reduced to give a compound of the formula I or Ia.

11. A compound of the formula XIII, XIIIa, XIIIb and XIIIc in the form of a racemate, a mixture of diastereomers or in essentially enantiomerically pure form,

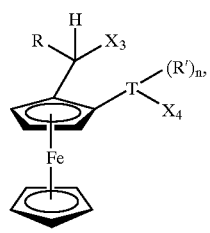
(XIII)

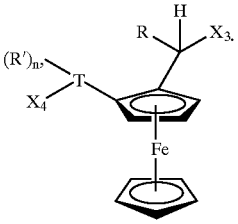
(XIIIa)

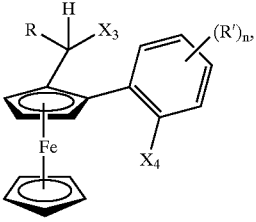
(XIIIb)

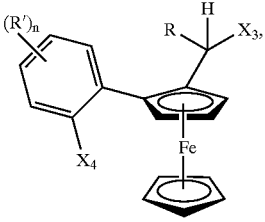
(XIIIc)

where
R is hydrogen, $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups;
n is 0 or an integer from 1 to 4 and R' are identical or different substituents selected from the group consisting of $C_1$–$C_4$alkyl, $C_1$–$C_4$fluoroalkyl and $C_1$–$C_4$alkoxy; and
a) $X_3$ is a secondary amino group A and $X_4$ is bromine, I or the group $X_2$=O;
b) $X_3$ is a secondary phosphino group $X_1$ and $X_4$ is the group $X_2$=O; or
c) R is $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups, $X_3$ is a secondary amino group A and $X_4$ is the group $X_2$;
$X_2$ is secondary phosphino;
T is $C_6$–$C_{20}$arylene or $C_3$–$C_{16}$heteroarylene;
and $X_2$ is found in the ortho position relative to the T-cyclopentadienyl bond.

12. A complex of a metal selected from the group consisting of the transition metals of Group 8 with a compound according to claim 1 as a ligand.

13. A metal complex according to claim 12, wherein the metal is selected from the group consisting of Cu, Ag, Au, Ni, Co, Rh, Pd, Ir and Pt.

14. A metal complex according to claim 12, wherein the metal is selected from the group consisting of rhodium, iridium, ruthenium, platinum and palladium.

15. A metal complex according to claim 12 which has the formula XIV or XV, $$A_1MeL_n \text{(XIV)}, \quad (A_1MeL_n)^{(z+)}(E^-)_z \quad \text{(XV)},$$

where $A_1$ is a compound of the formula I or Ia;

L are identical or different monodentate, anionic or nonionic ligands, or two L together form identical or different bidentate, anionic or nonionic ligands;

n is 2, 3 or 4 when L is a monodentate ligand, or n is 1 or 2 when L is a bidentate ligand;

z is 1, 2 or 3;

Me is a metal selected from the group consisting of Rh, Ir and Ru, with the metal having an oxidation state of 0, 1, 2, 3 or 4;

$E^-$ is the anion of an oxo acid or complex acid; and the anionic ligands balance the charge of the metal in the oxidation state 1, 2, 3 or 4.

16. A metal complex according to claim 12 which has the formula XVI or XVII, $$[A_1ME_1YZ](XVI), [A_1ME_1Y]^+E_1^- \quad (XVII),$$

where $A_1$ is a compound of the formula I or Ia;

$Me_1$ is rhodium or iridium;

Y is two olefins or one diene;

Z is Cl, Br or I; and $E_1^-$ is the anion of an oxo acid or complex acid.

17. A metal complex according to claim 16, wherein Y is two ethylenes or one 1,5-hexadiene, 1,5-cyclooctadiene or norbornadiene.

18. A metal complex according to claim 16, wherein Z is Cl or Br.

19. A metal complex according to claim 16, wherein $E_1$ is $ClO_4^{31}$, $CF_3SO_3^-$, $CH_3SO_3^-$, $HSO_4^-$, $BF_4^{31}$, $B(phenyl)_4^-$, $B(C_6F_5)_4^-$, $B(3,5\text{-bistrifluoromethylphenyl})_4^-$, $PF_6^-$, $SbCl_6^-$, $AsF_6^-$ or $SbF_6^-$.

20. A process for preparing chiral organic compounds by asymmetric addition of hydrogen, boron hydrides or silanes onto a carbon-carbon or carbon-heteroatom multiple bond in prochiral organic compounds or the asymmetric addition of carbon nucleophiles, alcohols or amines onto allyl compounds in the presence of a catalyst, wherein the addition reaction is carried out in the presence of catalytic amounts of at least one metal complex of the formula I or Ia according to claim 1.

21. A compound according to claim 2, wherein R is hydrogen, $C_1$–$C_4$alkyl, cyclopentyl, cyclohexyl or phenyl.

22. A compound according to claim 1 which has the formula If or Ig,

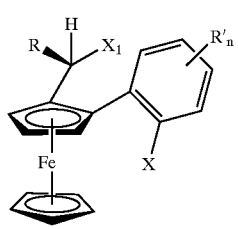

(If)

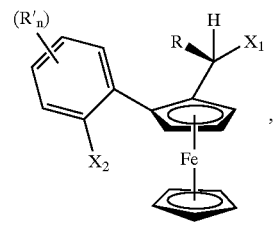

(Ig)

where R is $C_1$–$C_8$alkyl, $C_5$–$C_{12}$cycloalkyl, phenyl or phenyl substituted by from 1 to 3 $C_1$–$C_4$alkyl or $C_1$–$C_4$alkoxy groups, and T, R', n, $X_1$ and $X_2$ are as defined in claim 1.

23. A compound according to claim 9, wherein $R_1$ and $R_2$ as well as $R_3$ and $R_4$ or $R_1$, $R_2$, $R_3$ and $R_4$ are identical radicals.

24. A process for preparing a compound of the formula I according to claim 1, wherein a) a compound of the formula II

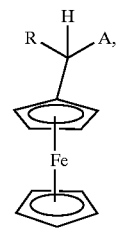

(II)

where R is as defined in claim 1 and A is secondary amino, is firstly reacted with a lithium alkyl, the reaction mixture is treated with a zinc dihalide, and is then reacted in the presence of Pd(0) or Pd(II) complexes as catalyst with a compound of the formula

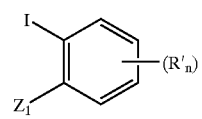

where R' and n are as defined in claim 1 and $Z_1$ is F, Cl, Br or I, to form a compound of the formula IIIa,

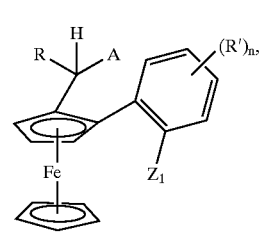

(IIIa)

b) the compound of the formula IIIa is reacted firstly with a lithium alkyl and then with a secondary halophosphine $X_2Cl$ or $X_2Br$ to form a compound of the formula IVa, where $X_2$ is as defined in claim 1,

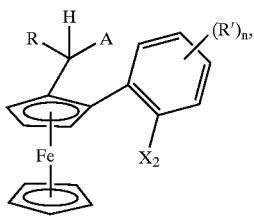
(IVa)

c) the phosphine group of the compound of the formula IVa is oxidised to form a compound of the formula Va,

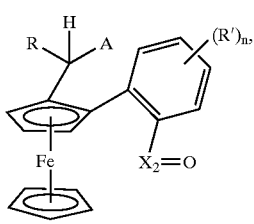
(Va)

d) the oxidised compound of the formula Va is reacted in the presence of an acid with a secondary phosphine $X_1H$, where $X_1$ is as defined in claim 1, to form a compound of the formula VIa,

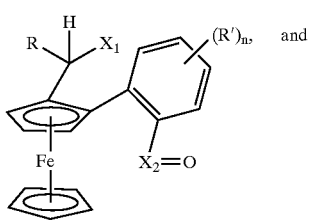
(VIa) and e) the $X_2{=}O$ group in the compound of the formula VIa is reduced to give a compound of the formula I or Ia.

25. A process according to claim 10, wherein the zinc dihalide is zinc dichloride.

26. A process according to claim 24, wherein the zinc dihalide is zinc dichloride.

27. A process according to claim 10, wherein $Z_1$ is Br.

28. A process according to claim 24, wherein $Z_1$ is Br.

29. A process according to claim 10, wherein the secondary halophosphine $X_2Cl$ or $X_2Br$ is $R_3R_4PCl$ or $R_3R_4PBr$, where $R_3$ and $R_4$ are each, independently of one another, a hydrocarbon radical which has from 1 to 20 carbon atoms and is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3$Si, $(C_1$–$C_{12}$-alkyl$)_3$Si, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

30. A process according to claim 24, wherein the secondary halophosphine $X_2Cl$ or $X_2Br$ is $R_3R_4PCl$ or $R_3R_4PBr$, where $R_3$ and $R_4$ are each, independently of one another, a hydrocarbon radical which has from 1 to 20 carbon atoms and is unsubstituted or substituted by halogen, $C_1$–$C_6$alkyl, $C_1$–$C_6$haloalkyl, C–$C_6$alkoxy, C–$C_6$haloalkoxy, $(C_6H_5)_3$Si, $(C_1$–$C_{12}$-alkyl$)_3$Si, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

31. A process according to claim 10, wherein the secondary phosphine $X_1H$ is $R_1R_2PH$, wherein $R_1$ and $R_2$ are each, independently of one another, a hydrocarbon radical which has from 1 to 20 carbon atoms and is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3$Si, $(C_1$–$C_{12}$-alkyl$)_3$Si, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

32. A process according to claim 24, wherein the secondary phosphine $X_1H$ is $R_1R_2PH$, wherein $R_1$ and $R_2$ are each, independently of one another, a hydrocarbon radical which has from 1 to 20 carbon atoms and is unsubstituted or substituted by halogen, $C_1$–$C_6$alkyl, $C_1$–$C_6$haloalkyl, $C_1$–$C_6$alkoxy, $C_1$–$C_6$haloalkoxy, $(C_6H_5)_3$Si, $(C_1$–$C_{12}$-alkyl$)_3$Si, or —$CO_2$—$C_1$–$C_6$-alkyl; or $R_1$ and $R_2$ and/or $R_3$ and $R_4$ in each case together form an unsubstituted or $C_1$–$C_4$alkyl- or $C_1$–$C_4$alkoxy-substituted dimethylene, trimethylene, tetramethylene, or pentamethylene group.

\* \* \* \* \*